US009823217B2

(12) United States Patent
Fife et al.

(10) Patent No.: US 9,823,217 B2
(45) Date of Patent: Nov. 21, 2017

(54) CHEMICAL DEVICE WITH THIN CONDUCTIVE ELEMENT

(71) Applicant: LIFE TECHNOLOGIES CORPORATION, Carlsbad, CA (US)

(72) Inventors: Keith G. Fife, Palo Alto, CA (US); Jordan Owens, Austin, TX (US); Shifeng Li, Fremont, CA (US); James Bustillo, Castro Valley, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 15/014,802

(22) Filed: Feb. 3, 2016

(65) Prior Publication Data

US 2016/0153930 A1    Jun. 2, 2016

Related U.S. Application Data

(63) Continuation of application No. 14/198,402, filed on Mar. 5, 2014, now abandoned.

(60) Provisional application No. 61/868,942, filed on Aug. 22, 2013, provisional application No. 61/790,866, filed on Mar. 15, 2013.

(51) Int. Cl.
*G01N 27/414*   (2006.01)
*B01L 3/00*   (2006.01)

(52) U.S. Cl.
CPC ...... *G01N 27/414* (2013.01); *B01L 3/502761* (2013.01); *G01N 27/4148* (2013.01); *B01L 2200/0668* (2013.01); *B01L 2300/0636* (2013.01); *B01L 2300/0877* (2013.01); *G01N 27/4145* (2013.01)

(58) Field of Classification Search
CPC ............. G01N 27/414; G01N 27/4148; G01N 27/4145; G01N 27/4146; B01L 3/502761
See application file for complete search history.

(56) References Cited

U.S. PATENT DOCUMENTS 4,086,642  A    4/1978  Yoshida et al.
4,411,741  A    10/1983 Janata
(Continued)

FOREIGN PATENT DOCUMENTS

CN    1582334    2/2005
CN    1585896    2/2005
(Continued)

OTHER PUBLICATIONS

[No Author Listed], "ISFET Wikipedia article", *Wikipedia*, Last modified Nov. 7, 2006, 2006.
(Continued)

*Primary Examiner* — Karen Kusumakar
(74) *Attorney, Agent, or Firm* — John Schell

(57) ABSTRACT

In one implementation, a chemical device is described. The sensor includes a chemically-sensitive field effect transistor including a floating gate structure having a plurality of floating gate conductors electrically coupled to one another. A conductive element overlies and is in communication with an uppermost floating gate conductor in the plurality of floating gate conductors. The conductive element is wider and thinner than the uppermost floating gate conductor. A dielectric material defines an opening extending to an upper surface of the conductive element.

20 Claims, 15 Drawing Sheets

(56) References Cited

U.S. PATENT DOCUMENTS

| | | |
|---|---|---|
| 4,437,969 A | 3/1984 | Covington et al. |
| 4,438,354 A | 3/1984 | Haque et al. |
| 4,444,644 A | 4/1984 | Hiramoto |
| 4,490,678 A | 12/1984 | Kuisl et al. |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Litenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,126,759 A | 6/1992 | Small et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,929,944 B2 | 8/2005 | Matson |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,091,059 B2 | 8/2006 | Rhodes |
| 7,097,973 B1 | 8/2006 | Zenhausern |
| 7,105,300 B2 | 9/2006 | Parce et al. |
| 7,106,089 B2 | 9/2006 | Nakano et al. |
| 7,173,445 B2 | 2/2007 | Fujii et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |

(56) References Cited

U.S. PATENT DOCUMENTS

| | | |
|---|---|---|
| 7,235,389 B2 | 6/2007 | Lim et al. |
| 7,238,323 B2 | 7/2007 | Knapp et al. |
| 7,244,559 B2 | 7/2007 | Rothberg et al. |
| 7,244,567 B2 | 7/2007 | Chen |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,817 B2 | 11/2009 | Tay |
| 7,614,135 B2 | 11/2009 | Santini, Jr. et al. |
| 7,667,501 B2 | 2/2010 | Surendranath et al. |
| 7,733,401 B2 | 6/2010 | Takeda |
| 7,785,790 B1 | 8/2010 | Church et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,885,490 B2 | 2/2011 | Heideman et al. |
| 7,888,708 B2 | 2/2011 | Yazawa et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,067,731 B2 | 11/2011 | Matyjaszczyk et al. |
| 8,072,188 B2 | 12/2011 | Yorinobu et al. |
| 8,124,936 B1 | 2/2012 | Lagna |
| 8,133,698 B2 | 3/2012 | Silver |
| 8,138,496 B2 | 3/2012 | Li et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,415,716 B2 | 4/2013 | Rothberg et al. |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rockenschaub et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,841,217 B1 | 9/2014 | Fife et al. |
| 8,847,637 B1 | 9/2014 | Guyton |
| 8,912,005 B1 | 12/2014 | Fife et al. |
| 8,936,763 B2 | 1/2015 | Rothberg et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,201,041 B2 | 12/2015 | Dalton et al. |
| 9,270,264 B2 | 2/2016 | Jordan et al. |
| 9,389,199 B2 | 7/2016 | Cheng et al. |
| 9,458,502 B2 | 10/2016 | Rothberg et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0012937 A1 | 1/2002 | Tender et al. |
| 2002/0029971 A1 | 3/2002 | Kovacs |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0081714 A1 | 6/2002 | Jain et al. |
| 2002/0085136 A1 | 7/2002 | Moon et al. |
| 2002/0086318 A1 | 7/2002 | Manalis et al. |
| 2002/0094533 A1 | 7/2002 | Hess et al. |
| 2002/0117694 A1 | 8/2002 | Migliorato et al. |
| 2002/0150909 A1 | 10/2002 | Stuelpnagel et al. |

(56) References Cited

U.S. PATENT DOCUMENTS

| | | |
|---|---|---|
| 2002/0168678 A1 | 11/2002 | Williams et al. |
| 2003/0020334 A1 | 1/2003 | Nozu et al. |
| 2003/0032052 A1 | 2/2003 | Hadd et al. |
| 2003/0044799 A1 | 3/2003 | Matson |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0152929 A1 | 8/2003 | Howard |
| 2003/0152994 A1 | 8/2003 | Woudenberg et al. |
| 2003/0155942 A1 | 8/2003 | Thewes |
| 2003/0175990 A1 | 9/2003 | Hayenga et al. |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2004/0002470 A1 | 1/2004 | Keith et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti |
| 2005/0058990 A1 | 3/2005 | Guia et al. |
| 2005/0062093 A1 | 3/2005 | Sawada et al. |
| 2005/0093645 A1 | 5/2005 | Watanabe et al. |
| 2005/0106587 A1 | 5/2005 | Klapproth et al. |
| 2005/0142033 A1 | 6/2005 | Glezer et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2005/0285155 A1 | 12/2005 | Johnson et al. |
| 2006/0000772 A1 | 1/2006 | Sano et al. |
| 2006/0035400 A1 | 2/2006 | Wu et al. |
| 2006/0040297 A1 | 2/2006 | Leamon et al. |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann, Jr. et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2006/0289726 A1 | 12/2006 | Paulus et al. |
| 2007/0059741 A1 | 3/2007 | Kamahori et al. |
| 2007/0069291 A1 | 3/2007 | Stuber et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0099208 A1 | 5/2007 | Drmanac et al. |
| 2007/0117099 A1 | 5/2007 | Engelhardt et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0094074 A1 | 4/2008 | Kim et al. |
| 2008/0096216 A1 | 4/2008 | Quake |
| 2008/0111161 A1 | 5/2008 | Sorge et al. |
| 2008/0115361 A1 | 5/2008 | Santini et al. |
| 2008/0121946 A1 | 5/2008 | Youn et al. |
| 2008/0136933 A1 | 6/2008 | Dosluoglu et al. |
| 2008/0145910 A1 | 6/2008 | Ward |
| 2008/0164917 A1 | 7/2008 | Floyd et al. |
| 2008/0176271 A1 | 7/2008 | Silver et al. |
| 2008/0185616 A1 | 8/2008 | Johnson et al. |
| 2008/0197022 A1 | 8/2008 | Suzuki et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0026082 A1 | 1/2009 | Rothberg et al. |
| 2009/0030117 A1 | 1/2009 | Lanphere et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0075838 A1 | 3/2009 | El Gamal et al. |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127589 A1 | 5/2009 | Rothberg |
| 2009/0127689 A1 | 5/2009 | Ye et al. |
| 2009/0140763 A1 | 6/2009 | Kim |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0201032 A1 | 8/2009 | Burdett et al. |
| 2009/0273386 A1 | 11/2009 | Korobeynikov et al. |
| 2010/0007326 A1 | 1/2010 | Nakazato |
| 2010/0026814 A1 | 2/2010 | Shimoda |

(56) References Cited

U.S. PATENT DOCUMENTS

| | | |
|---|---|---|
| 2010/0039146 A1 | 2/2010 | Park et al. |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0156454 A1 | 6/2010 | Weir |
| 2010/0176463 A1 | 7/2010 | Koizumi et al. |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0273166 A1 | 10/2010 | Garcia |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0248320 A1 | 10/2011 | Rothberg et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife et al. |
| 2012/0001056 A1 | 1/2012 | Fife et al. |
| 2012/0001235 A1* | 1/2012 | Fife ................ G01N 27/414 257/253 |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001779 A1 | 1/2012 | Fife et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0060587 A1 | 3/2012 | Babcock et al. |
| 2012/0067723 A1 | 3/2012 | Rearick et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0173159 A1 | 7/2012 | Davey et al. |
| 2012/0228136 A1 | 9/2012 | Levine |
| 2012/0247977 A1 | 10/2012 | Rothberg et al. |
| 2012/0249192 A1 | 10/2012 | Matsushita et al. |
| 2012/0261274 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew et al. |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |
| 2013/0105868 A1 | 5/2013 | Kalnitsky et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0308752 A1 | 10/2014 | Chang et al. |
| 2015/0097214 A1 | 4/2015 | Chen et al. |
| 2016/0178568 A1 | 6/2016 | Cheng et al. |

FOREIGN PATENT DOCUMENTS

| | | |
|---|---|---|
| CN | 1703623 | 11/2005 |
| CN | 1826525 | 8/2006 |
| CN | 101669026 | 3/2010 |
| CN | 101676714 | 3/2010 |
| CN | 102203282 | 9/2011 |
| CN | 102301228 | 12/2011 |
| CN | 102484267 | 5/2012 |
| DE | 4232532 | 4/1994 |
| DE | 4430811 | 9/1995 |
| DE | 19512117 | 10/1996 |
| DE | 102004044299 | 3/2006 |
| DE | 102008012899 | 9/2009 |
| EP | 0223618 | 5/1987 |
| EP | 1243925 | 9/2002 |
| EP | 1243925 | 3/2003 |
| EP | 1371974 | 12/2003 |
| EP | 1432818 | 6/2004 |
| EP | 1542009 | 6/2005 |
| EP | 1557884 | 7/2005 |
| EP | 1669749 | 6/2006 |
| EP | 1975246 | 3/2007 |
| EP | 1870703 | 12/2007 |
| EP | 2307577 | 4/2011 |
| GB | 2457851 | 9/2009 |
| GB | 2461127 | 12/2009 |
| GB | 2461127 B | 7/2010 |
| JP | 58070155 | 4/1983 |
| JP | 62-237349 | 10/1987 |
| JP | 02-250331 | 10/1990 |
| JP | 02-310931 | 12/1990 |
| JP | H05-080155 | 4/1993 |
| JP | 2000055874 | 2/2000 |
| JP | 2002-221510 | 8/2002 |
| JP | 2002/272463 | 9/2002 |
| JP | PCT/JP2003/04697 | 4/2003 |
| JP | 2003-279532 | 10/2003 |
| JP | 2003-322633 | 11/2003 |
| JP | 2004-510125 | 4/2004 |
| JP | 2005218310 | 8/2004 |
| JP | 2004-271384 | 9/2004 |
| JP | 2005/077210 | 3/2005 |
| JP | 2005077210 | 3/2005 |
| JP | 2005-515475 | 5/2005 |
| JP | 2005-518541 | 6/2005 |

(56) References Cited

FOREIGN PATENT DOCUMENTS

| | | |
|---|---|---|
| JP | 2005-207797 | 8/2005 |
| JP | 2006138846 | 6/2006 |
| JP | 2006-284225 | 10/2006 |
| JP | 2007/243003 | 9/2007 |
| JP | 2008-215974 | 9/2008 |
| JP | 2010513869 | 4/2010 |
| JP | 2011-525810 | 9/2011 |
| JP | 2011525810 | 9/2011 |
| JP | 2012-506557 | 3/2012 |
| JP | 2015-506557 | 3/2012 |
| KR | 100442838 | 8/2004 |
| KR | 10-0455283 | 10/2004 |
| KR | 100455283 | 11/2004 |
| TW | 200946904 | 11/2009 |
| WO | 89/09283 | 10/1989 |
| WO | WO-1990/005910 | 5/1990 |
| WO | 98/13523 | 4/1998 |
| WO | 98/46797 | 10/1998 |
| WO | 01/20039 | 3/2001 |
| WO | 01/42498 | 6/2001 |
| WO | 01/47804 | 7/2001 |
| WO | 01/81896 | 11/2001 |
| WO | 02/077287 | 10/2002 |
| WO | 02/086162 | 10/2002 |
| WO | 03/073088 | 9/2003 |
| WO | 2004/017068 | 2/2004 |
| WO | 2004/040291 | 5/2004 |
| WO | 2004/048962 | 6/2004 |
| WO | WO-2004/081234 | 9/2004 |
| WO | 2005/015156 | 2/2005 |
| WO | 2005/022142 | 3/2005 |
| WO | 2005/043160 | 5/2005 |
| WO | 2005/047878 | 5/2005 |
| WO | 2005/054431 | 6/2005 |
| WO | 2005062049 | 7/2005 |
| WO | 2005/073706 | 8/2005 |
| WO | 2005/084367 | 9/2005 |
| WO | 2005/090961 | 9/2005 |
| WO | 2005090961 | 9/2005 |
| WO | 2006/005967 | 1/2006 |
| WO | 2006/022370 | 3/2006 |
| WO | 2006/056226 | 6/2006 |
| WO | 2007002204 | 1/2007 |
| WO | 2007/086935 | 8/2007 |
| WO | 2008/007716 | 1/2008 |
| WO | 2008/058282 | 5/2008 |
| WO | 2008/076406 | 6/2008 |
| WO | 2008076406 | 6/2008 |
| WO | 2008/107014 | 9/2008 |
| WO | 2008/133719 | 11/2008 |
| WO | 2009/012112 | 1/2009 |
| WO | WO-2009/014155 | 1/2009 |
| WO | 2009/041917 | 4/2009 |
| WO | 2009/074926 | 6/2009 |
| WO | 2009/081890 | 7/2009 |
| WO | 2009/158006 | 12/2009 |
| WO | 2010/008480 | 1/2010 |
| WO | 2010/047804 | 4/2010 |
| WO | 2010/138182 | 12/2010 |
| WO | 2010/138186 | 12/2010 |
| WO | 2010/138188 | 12/2010 |
| WO | 2012/003359 | 1/2012 |
| WO | 2012/003363 | 1/2012 |
| WO | 2012/003368 | 1/2012 |
| WO | 2012/003380 | 1/2012 |
| WO | 2012/006222 | 1/2012 |
| WO | 2012/046137 | 4/2012 |
| WO | 2012/152308 | 11/2012 |
| WO | 2014/077783 | 5/2014 |

OTHER PUBLICATIONS

Ahmadian, et al., "Single-nucleotide polymorphism analysis by pyrosequencing", *Anal. Biochem*, vol. 280, 2000, 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767, , "Search Information Statement", Oct. 26, 2011, pp. 1-3.
Bandiera, L. et al., "A fully electronic sensor for the measurement of cDNA hybridization kinetics", *Biosens Bioelectron*, vol. 22, 2007, pp. 2108-2114.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M. et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M. et al., "Fully electronic DNA hybridization detection by a standard CMOS biochip", *Sensors and Actuators B Chemical*, vol. 118, 2006, 41-46.
Bashford, G. et al., "Automated bead-trapping apparatus and control system for single-molecule DNA sequencing", *Optics Express*, vol. 16(5), Mar. 3, 2008, pp. 3445-3455.
Baumann, W. et al., "Microelectronic sensor system for microphysiological application on living cells", *Sensors Actuators B*, vol. 55, 1999, pp. 77-89.
Bausells, J. et al., "Ion-sensitive field-effect transistors fabricated in a commercial CMOS technology", *Sensors and Actuators B Chemical*, vol. 57, 1999, pp. 56-62.
Bergveld, , "ISFET, Theory and Practice", *IEEE Sensor Conference, Toronto, Oct. 2003*, 2003, pp. 1-26.
Bergveld, , "Thirty years of ISFETOLOGY What happened in the past 30 years and what may happen in the next 30 years", *Sensors and Actuators B*, vol. 88, 2003, pp. 1-20.
Besselink, et al., "ISFET Affinity Sensor", *Methods in Biotechnology, vol. 7: Affinity Biosensors: Techniques and Protocols*, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.
Bockelmann, U. et al., "Detecting DNA by field effect transistor arrays", *Proceedings of the 2006 IFIP International Conference on Very Large Scale Integration*, 2006, 164-168.
Bousse, L. et al., "A process for the combined fabrication of ion sensors and CMOS circuits", *IEEE Electron Device Letters*, vol. 9(1), 1988, pp. 44-46.
Bousse, L. et al., "Zeta potential measurements of Ta2O5 and SiO2 thin films" *J. Colloid Interface Sci.*, vol. 147(1), 1991, pp. 22-32.
Chan, Wai P. et al., "An Integrated ISFETs Instrumentation System in Standard CMOS Technology", *IEEE Journal of Solid-State Circuits*, vol. 45, No. 9, Sep. 2010, pp. 1923-1934.
Chen, Y. et al., "Nanoscale field effect transistor for biomolecular signal amplification", *App Phys Letter*, vol. 91, 2007, pp. 243511-1-243511-3.
Chen, Y. et al., "Silicon-based nanoelectronic field-effect pH sensor with local gate control", *App Phys Letter*, vol. 89, 2006, pp. 223512-1-223512-3.
Chin, Yuan-Lung et al., "Titanium Nitride Membrane Application to Extended Gate Field Effect Transistor pH Sensor Using VLSI Technology", *Jpn. J. Appl. Phys.* vol. 40, Part 1, No. 11, Nov. 2001, pp. 6311-6315.
Chou, J. et al., "Letter to the Editor on Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-76.
Chung, et al., "ISFET interface circuit embedded with noise rejection capability", *Electronics Letters*, vol. 40, No. 18, Oct. 2004, 1115-1116.
Chung, W-Y et al., "ISFET performance enhancement by using the improved circuit techniques", *Sensors and Actuators B*, vol. 113, 2006, pp. 555-562.

(56) References Cited

OTHER PUBLICATIONS

Chung, W-Y et al., "New ISFET interface circuit design with temperature compensation", *Microelectronics Journal*, vol. 37(10), Oct. 1, 2006, pp. 1105-1114.
Chung, W-Y et al., "Temperature compensation electronics for ISFET readout applications", *Biomedical Circuits and Systems*, IEEE International Workshop Singapore, Dec. 1, 2004, pp. 305-308.
Dazhong, Z. et al., "Research of CMOS Biosensor IC for Extracellular Electrophysiological Signal Recording and pH value Measuring", *Solid-State and Integrated-Circuit Technology, 9th International Conference*, NJ USA, Oct. 20, 2008, pp. 2557-2560.
Dorf, Richard C. , "The Electrical Engineering Handbook", *University of California, Davis, CRC Press, 2 edition, Chaster 3—Linear Circuit Analysis*, Jun. 25, 2004, pp. 3-1 to 3-66.
Eijkel, J. et al., "Measuring Donnan-related phenomena using a solid-state ion sensor and a concentration-step method", *J. Membrane Sci.*, vol. 127, 1997, pp. 203-221.
Eijkel, J. , "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662 .
EP09798251.6, "Extend European Search Report" mailed Aug. 27, 2013, 6 pages.
EP09822323.3, "European Extended Search Report" mailed May 27, 2015, 8 pages.
EP10780930, "European Search Report" mailed Jun. 15, 2015, 3 pages.
EP10780935, "European Search Report" mailed Jun. 9, 2015, 5 pages.
EP10780935, "Supplementary European Search Report" mailed Sep. 30, 2015, 6 pages.
EP10857377, "European Search Report" mailed Jun. 26, 2015, 3 pages.
EP11801437.2, "European Extended Search Report" mailed Jul. 25, 2013, 10 pages.
EP11801437.2, "LT00349EP Examination Notification" mailed Feb. 12, 2015, 8 pages.
EP11801439.8, "Extended Search Report" mailed Mar. 7, 2014, 9 pages.
EP11804218.3, "European Extended Search Report" mailed Jul. 11, 2013, 3 pages.
EP11827128.7, "European Search Report" mailed Aug. 1, 2013, 5 pages.
EP13161312.7, "Extend European Search Report" mailed Oct. 15, 2013, 8 pages.
EP13163995.7, "EP Search Report" mailed Jul. 9, 2014.
EP13163995.7, "Extend European Search Report" mailed Aug. 20, 2013, 6 pages.
EP13164768.7, "European Search Report" mailed Aug. 20, 2013, 6 pages.
EP13174555.6, "EP Extended Search Report" mailed Dec. 12, 2013, 8 pages.
EP13174555.6, "EP Search Report" mailed Nov. 21, 2013, 5 pages.
EP13177039.8, "EP Search Report" mailed Nov. 21, 2013, 9 pages.
EP13177590.0, "EP Search Report" mailed Nov. 20, 2013, 5 pages.
EP13177590.0, "European Examination Notification" mailed Sep. 8, 2014, 9 pages.
EP14152861.2, "EP Search Report" mailed Jul. 7, 2014, 5 pages.
EP15170247.9, "European Search Report" mailed Nov. 10, 2015, 4 pages.
EP7867780.4, "Examination Report" mailed Jul. 3, 2012.
Eriksson, J. et al., "Pyrosequencing technology at elevated temperature", *Electrophoresis*, vol. 25, 2004, pp. 20-27
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.
Eversmann, B. et al., "A 128×128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J. , "Handbook of Modern Sensors—Physics, Designs, and Applications . . . ", *17.3.2 CHEMFET Sensors*, 1996, pp. 499-501
Fritz, J. et al., "Electronic detection of DNA by its intrinsic molecular charge", *PNAS*, vol. 99, No. 22, Oct. 2002, 14142-14146

Gardner, J.W. et al., "Enhancing electronic nose performance by sensor selection using a new integer-based genetic algorithm approach", *Science Direct, Sensors and Actuators B*, vol. 106, 2005, pp. 114-121
GB0811656.8, "Search and Examination Report" mailed Mar. 12, 2010.
GB0811656.8, "Search Report" mailed Sep. 21, 2009.
GB0811657.6, "Examination Report" mailed Jun. 30, 2010.
GB0811657.6, "Search Report under Section 17" mailed Oct. 26, 2009.
Gracia, I. et al., "Test Structures for ISFET Chemical Sensors", *Proc IEEE 1992 Intl Conf Microelec Test Struct*, vol. 5, 1992, pp. 156-159 .
Hammond, et al., "Performance and system-on-chip integration of an unmodified CMOS ISFET", *Science Direct, Sensors and Actuators* vol. 111-112, 2005, pp. 254-258.
Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P. et al., "Design of a Single-Chip pH Sensor Using a Conventional 0.6-µm CMOS Process", *IEEE Sensors Journal*, vol. 4(6), 2004, 706-712.
Hammond, P. et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hamster ovary cell line using Illumina sequencing technology", *BMC Genomics*, vol. 12:67, 2011, pp. 1-8.
Han, Y , "Label-free detection of biomolecules by a field-effect transistor microarray biosensor with bio-functionalized gate surfaces", Masters Dissertation, 2006, pp. 1-63.
Hanshaw, R. et al., "An indicator displacement system for fluorescent detection of phosphate oxyanions under physiological conditions", *Science Direct, Tetrahedron Letters*, vol. 45, Nov. 15, 2004, pp. 8721-8724.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications" *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, et al., "Identification of a Single Nucleotide Polymorphism in the MXA Gene Promoter (T/T at nt-88) Correlated with the Response of Hepatitis C Patients to Interferon", *Intervirology*, vol. 43, 2000, 124-127.
Hizawa, et al., "Sensing Characteristics of Charge Transfer Type pH Sensor by Accumulative Operation", *IEEE Sensors, EXCO*, Daegu, Korea, Oct. 22-25, 2006, pp. 144-147.
Hizawa, T et al., "Fabrication of a two-dimensional pH image sensor using a charge transfer technique", *Sensors and Actuators B Chemical*, vol. 117, 2006, 509-515.
Hizawa, T. et al., "32×32 pH Image Sensors for Real Time Observation of Biochemical Phenomena", *Transducers & Eurosensors*

(56) References Cited

OTHER PUBLICATIONS

'07, 14th Intl. Conf. on Solid-State, Actuators and Microsystems, Lyon, France, Jun. 10-14, 2007, 2007, pp. 1311-1312.
Ingebrandt, Sven et al., "Label-free detection of DNA using field-effect transistors", *Phys. stat. sol. (a)* 203, No. 14, 2006, pp. 3399-3411.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS*, 2006, pp. 3357-3360.
Ji, H. et al., "Contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), 2004, pp. 69-74.
Klein, M. , "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Krause, M. et al., "Extended gate electrode arrays for extracellular signal recordings", *Sensors and Actuators B*, vol. 70, 2000, pp. 101-107.
Kruise, J. et al., "Detection of protein concentrations using a pH-step titration method", *Sensors Actuators B*, vol. 44, 1997, pp. 297-303.
Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.
Leamon, J. et al., "Cramming More Sequencing Reactions onto Microreactor Chips" *Chemical Reviews*, vol. 107, 2007, pp. 3367-3376.
Lee, C-S et al., "Ion-sensitive Field-Effect Transistor for Biological Sensing", *Sensors*, vol. 9, 2009, pp. 7111-7131.
Lee, S. et al., "An Enhanced Glucose Biosensor Using Charge Transfer Techniques", *Biosensors and Bioelectronics*, vol. 24, 2008, pp. 650-656.
Li, et al., "Sequence-Specific Label-Free DNA Sensors Based on Silico Nanowires", *Nano Letters,*, vol. 4, No. 2, 2004, 245-247.
Ligler, Frances S. et al., "Array biosensor for detection of toxins", *Anal. Bioanal Chem* vol. 377, 2003, pp. 469-477.
Lin, B.J. et al., "Practicing the Novolac deep-UV portable conformable masking technique", *Journal of Vacuum Science and technology*, Vo. 19, No. 4, 1981, 1313-1319.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proc. of the 1996 IEEE Intl. Conf. on Microelectronic Test Structures*, vol. 9, 1996, pp. 123-128.
Maki, W et al., "Nanowire-transistor based ultra-sensitive DNA methylation detection", *Biosensors & Bioelectronics*, 23, 2008, pp. 780-787.
Margulies, et al., "Genome sequencing in microfabricated high-density picolitre reactors", *Nature*, vol. 437 (15), Jul. 31, 2005, 376-380.
Marshall, et al., "DNA chips: an array of possibilities", *Nature Biotechnology*, vol. 16, 1998, 27-31.
Martinoia, S. et al., "A behavioral macromodel of the ISFET in SPICE", *Sensors Actuators B*, vol. 62, 2000, pp. 182-189.
Martinoia, S. et al., "Development of ISFET Array-Based Microsystems for Bioelectrochemical measurements of cell populations", *Biosensors & Bioelectronics*, vol. 16, 2001, pp. 1043-1050.
Matsuo, J. et al., "Charge Transfer Type pH Sensor with Super High Sensitivity", *the 14th international conference on solid-state sensors actuators and microsystems*, France, Jun. 10-14, 2007, pp. 1881-1884.
Matula, Richard A. , "Electrical Resistivity of Copper, Gold, Palladium, and Silver" *Journal of Physical and Chemical Reference Data*, vol. 8.4, 1979, pp. 1147-1298.
Medoro, G. et al., "A Lab-on-a-Chip for Cell Detection and Manipulation", *IEEE Sensors J*, vol. 3(3), 2003, pp. 317-325.
Meyburg, et al., "N-Channel field-effect transistors with floating gates for extracellular recordings", *Biosens Bioelectron*, vol. 21(7), 2006, pp. 1037-1044.
Milgrew, et al., "The fabrication of scalable multi-sensor arrays using stamdard CMOS technology", *2003 IEEE Custom Integrated Circuits Conference*, 2003, pp. 513-516.
Milgrew, M. et al., "A 16×16 CMOS proton camera array for direct extracellular imaging of hydrogen-ion activity", *IEEE Intl Solid-State Circuits Conf*, Session 32:24, 2008, pp. 590-591; 638.
Milgrew, M. et al., "A large transistor based sensor array chip for direct extracellular imaging", *Sensors and Actuators B Chemical*, vol. 111-112, 2005, 347-353.
Milgrew, M. et al., "Matching the transconductance characteristics of CMOS ESFET arrays by removing trapped charge", *IEEE Trans Electron Devices*, vol. 55(4), 2008, pp. 1074-1079.
Milgrew, M. et al., "Microsensor Array Technology for Direct Extracellular Imaging", Apr. 5, 2006, pp. 1-23.
Milgrew, M. et al., "The development of scalable sensor arrays using standard CMOS technology", *Sensors and Actuators B*, vol. 103, 2004, 37-42.
Milgrew, M.J. et al., "The development of scalable sensor arrays using standard CMOS technology", *ScienceDirect, Sensors and Actuators*, vol. 103, 2004, pp. 37-42.
Milgrew, Mark J. et al., "A Proton Camera Array Technology for Direct Extracellular Ion Imaging", *IEEE International Symposium on Industrial Electronics*, 2008, 2051-2055.
Miyahara, Y. et al., "Biochip Using Micromachining Technology", *J. Institute of Electrostatics*, Japan, vol. 27, No. 6, 2003, 268-272.
Miyahara, Y. et al., "Direct Transduction of Primer Extension into Electrical Signal Using Genetic Field Effect Transistor", *Micro Total Analysis Systems 2004*, vol. 1, 2004, pp. 303-305.
Miyahara, Y. et al., "Potentiometric Detection of DNA Molecules Using Field Effect Transistor", *The Japan Society of Applied Physics*, No. 3 (Translation included), 2003, 1180, 30A-S2.
Naidu, M. S. et al., "Introduction to Electrical Engineering", *Chapter 1—Fundamental Concepts of Electricity, McGraw Hill Education (India) Private Limited*, 1995, pp. 1-10.
Neaman, Donald A. , "Electronic Circuit Analysis and Design", *McGraw Hill Higher Education, 2nd edition, Chapter 6—Basic FET Amplifiers*, (reference will be uploaded in 2 parts due to size) part 1 of 2, Dec. 1, 2000, pp. 313-345.
Neaman, Donald A. , "Electronic Circuit Analysis and Design", *McGraw Hill Higher Education, 2nd Edition, Chapter 6—Basic FET Amplifiers*, (reference will be uploaded in 2 parts due to size) part 2 of 2, Dec. 1, 2000, pp. 346-381.
Nishiguchi, K. et al., "Si nanowire ion-sensitive field-effect transistors with a shared floating gate", *Applied Physics Letters vol. 94*, 2009, pp. 163106-1 to 163106-3.
Nyren, P. et al., "Enzymatic Method for Continuous Monitoring of Inorganic Pyrophosphate Synthesis", *Analytical Biochemistry*, vol. 151, 1985, pp. 504-509.
Oelbner, W. et al., "Encapsulation of ESFET sensor chips", *Sensors Actuators B*, vol. 105, 2005, pp. 104-117 .
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Palan, B. et al., "New ISFET sensor interface circuit for biomedical applications", *Sensors and Actuators B: Chemical: International Journal Devoted to Research and Development of Physical and Chemical Transducers, Elsevier S.A. Ch.*, vol. 57, No. 1-3, 1999, pp. 63-68.

(56) References Cited

OTHER PUBLICATIONS

Park, K-Y et al., "ISFET glucose sensor system with fast recovery characteristics by employing electrolysis", *Sensors and Actuators B: Chemical*, vol. 83 (1-3), Mar. 15, 2002, pp. 90-97.
Patolsky, F. et al., "Nanowire-Based Biosensors", *Analyt Chem 1*, vol. 78(13), 2006, pp. 4261-4269
PCT/JP2005/001987, "International Search Report" mailed Apr. 5, 2005.
PCT/JP2005/015522, "International Preliminary Report on Patentability", mailed Mar. 19, 2007.
PCT/JP2005/015522, "International Search Report", (includes English translation), mailed Sep. 27, 2005.
PCT/US/2009/05745, "International Preliminary Report on Patentability" mailed Apr. 26, 2011.
PCT/US/2009/05745, "International Search Report and Written Opinion", Mailed Dec. 11, 2009, 2009.
PCT/US2007/025721, "Declaration of Non-Establishment of International Search Report" mailed Jul. 15, 2008.
PCT/US2007/025721, "International Preliminary Report on Patentability" mailed Jun. 16, 2009.
PCT/US2007/025721, "Written Opinion" mailed Jun. 16, 2009.
PCT/US2009/003766, "International Preliminary Report on Patentability" mailed Jan. 5, 2011.
PCT/US2009/003766, "International Search Report and Written Opinion" mailed Apr. 8, 2010.
PCT/US2009/003797, "International Search Report and Written Opinion" mailed Mar. 12, 2010.
PCT/US2010/001543, "International Preliminary Report on Patentability" mailed Nov. 29, 2011, pp. 1-8.
PCT/US2010/001543, "International Search Report and Written Opinion" mailed Oct. 13, 2010, pp. 1-12.
PCT/US2010/001553, "International Preliminary Report on Patentability" mailed Dec. 8, 2011, pp. 1-10.
PCT/US2010/001553, "International Search Report and Written Opinion" mailed Jul. 28, 2010, pp. 1-2.
PCT/US2010/048835, "International Preliminary Report on Patentability" mailed Mar. 19, 2013, 7 pages.
PCT/US2010/48835, "International Search Report and Written Opinion" mailed Dec. 16, 2010, pp. 1-12.
PCT/US2011/042655, "International Search Report" mailed Oct. 21, 2011, pp. 1-2.
PCT/US2011/042660, "International Search Report" mailed Nov. 2, 2011.
PCT/US2011/042665, "International Search Report" mailed Nov. 2, 2011.
PCT/US2011/042668, "International Preliminary Report on Patentability" mailed Mar. 26, 2013, 11 pages.
PCT/US2011/042668, "International Search Report" mailed Oct. 28, 2011.
PCT/US2011/042669, "International Search Report and Written Opinion" mailed Jan. 9, 2012, pp. 1-5.
PCT/US2011/042683, "International Preliminary Report on Patentability" mailed Jun. 4, 2013, 5 pages.
PCT/US2011/042683, "International Search Report and Written Opinion" mailed Feb. 16, 2012.
PCT/US2012/058996, "International Search Report and Written Opinion" mailed Jan. 22, 2013, pp. 1-11.
PCT/US2012/071471, "International Preliminary Report on Patentability" mailed Jun. 24, 2014, 8 pages.
PCT/US2012/071471, "International Search Report of the International Searching Authority and Written Opinion" mailed Apr. 24, 2013, 14 pages.
PCT/US2012/071482, "International Preliminary Amendment" mailed Jun. 24, 2014, 7 pages.
PCT/US2012/071482, "International Search Report of the International Searching Authority and Written Opinion" mailed May 23, 2013, 11 pages.
PCT/US2013/022129, "International Preliminary Report on Patentability" mailed Jul. 22, 2014, 11 pages.
PCT/US2013/022129, "International Search Report of the International Searching Authority and Written Opinion" mailed Aug. 9, 2013, 18 pages.
PCT/US2013/022140, "International Preliminary Report on Patentability" mailed Jul. 22, 2014, 9 pages.
PCT/US2013/022140, "International Search Report of the International Searching Authority and Written Opinion" mailed May 2, 2013, 15 pages.
PCT/US2014/020887, "International Preliminary Report on Patentability" mailed Sep. 15, 2015, 8 pages.
PCT/US2014/020887, "International Search Report and Written Opinion" mailed May 30, 2014, 12 pages.
PCT/US2014/020892, "International Search Report and Written Opinion" mailed Jun. 3, 2014.
PCT/US2014/040923, "International Preliminary Report on Patentability" mailed Dec. 15, 2015, 8 pages.
PCT/US2014/040923, "International Search Report and Written Opinion" mailed Sep. 1, 2014, 14 pages.
Poghossian, A. et al., "Functional testing and characterization of ISFETs on wafer level by means of a micro-droplet cell", *Sensors.* vol. 6, 2006, pp. 397-404.
Pollack, J. et al., "Genome-wide analysis of DNA copy-numbe changes using cDNA microarrays", *Nature Genetics Nature America Inc.*, vol. 23, Sep. 1999, pp. 41-46.
Pourmand, N et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, et al., "Ultra-low power precision ISFET readout using global current feedback", *Electronic Letters*, vol. 42, No. 22, Oct. 2006, 1264-1265.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Drift Reduction in Ion-Sensitive FETs using correlated double sampling", *Electronics Letters*, vol. 43, No. 16, Aug. 2, 2007, 857 (2 pages).
Purushothaman, S. et al., "Protons and single nucleotide polymorphism detection: A simple use for the Ion Sensitive Field Effect Transistor", *Sensors and Actuators B Chemical*, vol. 114(2), 2006, pp. 964-968
Purushothaman, S. et al., "Towards Fast Solid State DNA Sequencing" *IEEE ISCAS 2002 Proceedings*, Circuits and Systems, vol. 4, 2002, pp. IV-169-IV-172.
Rodriguez-Villegas, E., "Solution to trapped charge in FGMOS transistors", *Electronics Letters*, vol. 39(19), 2003.
Ronaghi, M. et al., "A Sequencing Method Based on Real-Time Pyrophosphate", *Science*, vol. 281, 1998, 363-365.
Rothberg, J. et al., "An integrated semiconductor device enabling non-optical genome sequencing", *Nature*, vol. 475, No. 7356, Jul. 21, 2011, pp. 348-352.
Rowe, Chris A. et al., "An Array Immunosensor for Simultaneous Detection of Clinical Analytes", *Anal. Chem.* vol. 71, 1999, pp. 433-439.
Sakata, et al., "Potentiometric Detection of DNA Using Genetic Transistor" *Denki Gakkai Kenkyukai Shiryo Chemical Sensor Kenkyukai*, CHS-03-51-55, 2003, 1-5.
Sakata, T. et al., "Cell-based field effect devices fo cell adhesion analysis", *Intl. Conf. on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proc. of 2006 Intl. Conf. on Microtechnologies in Medicine and Biology*, May 9-12, 2005, Okinawa, Japan, 2006, pp. 97-100.
Sakata, T. et al., "Direct detection of single nucleotide polymorphism using genetic field effect transistor", *Digest of Papers*

(56) References Cited

OTHER PUBLICATIONS

*Microprocesses and Nanotechnology* 2004, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, 2005, pp. 219-222.
Sakata, T. et al., "Direct transduction of allele-specific primer extension into electrical signal using genetic field effect transistor", *Biosensors and Bioelectronics*, vol. 22, 2007, pp. 1311-1316.
Sakata, T. et al., "DNA Analysis Chip Based on Field-Effect Transistors" *Japanese Journal of Applied Physics*, vol. 44(4B), 2005, pp. 2854-2859.
Sakata, T. et al., "DNA Sequencing Based on Intrinsic Molecular Charges", *Angewandte Chemie International Edition 2006*, vol. 118, 2006, 2283-2286.
Sakata, T. et al., "DNA Sequencing Based on Intrinsic Molecular Charges", *Angewandte Chemie International Edition 2006*, vol. 45, 2006, pp. 2225-2228.
Sakata, T. et al., "DNA Sequencing Using Genetic Field Effect Transistor" *13th Intl. Conf. on Solid-State Sensors, Actuators and Microsystems*, Jun. 5-9, 2005, Seoul, Korea, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832
.
Sakata, T. et al., "Potential Behavior of Biochemically Modified Gold Electrode for Extended-Gate Field-Effect Transistor", *Japanese Journal of Applied Physics*, vol. 44(4B), 2005, pp. 2860-2863.
Sakata, T. et al., "Potential Response of Genetic Field Effect Transistor to Charged Nanoparticle-DNA Conjugate", *Digest of Papers Microprocesses and Nanotechnology 2005*, Tokyo, Japan, 2005 Intl Microprocesses and Nanotech Conference, Hotel Bellclassic, 2005, pp. 42-43.
Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.
Sakata, T. et al., "Potentiometric Detection of Single Nucleotide Polymorphism by Using a Genetic Field-effect transistor", *ChemBioChem*, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", *Thesis*, Presented at Stanford University, 2005, pp. ii-78.
Salama, K., "Modeling and simulation of luminescence detection platforms", *Biosensors & Bioelectronics*, 2004, pp. 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72
.
Schasfoort, R. et al., "A new approach to immunoFET operation", *Biosensors & Bioelectronics*, vol. 5, 1990, pp. 103-124.
Schasfoort, R. et al., "Field-effect flow control for microfabricated fluidic networks", *Science*, vol. 286(5441), 1999, pp. 942-945.
Schoning, M. et al., "Bio FEDs (Field-Effect Devices): State-of-the-Art and New Directions", *Electroanalysis*, vol. 18(19-20), 2006, pp. 1893-1900.
Seong-Jin, K. et al., "Label-Free CMOS DNA Quantification With On-Chip Noise Reduction Schemes", *Solid-State Sensors, Actuators and Microsystems Conference, IEEE*, Jun. 10, 2013, pp. 947-950.
SG200903992-6, , "Search and Examination Report (Favourable) Mailed Jan. 20, 2011", 12.
Shah, N., "Microfabrication of a parellel-array DNA pyrosequencing chip", NNIN REU Research Accomplishments, 2005, pp. 130-131.
Shepherd, L. et al., "A biochemical translinear principle with weak inversion ISFETs", *IEEE Trans Circuits Syst-I*, vol. 52(12), Dec. 2005, pp. 2614-2619.
Shepherd, L. et al., "A novel voltage-clamped CMOS ISFET sensor interface", *IEEE*, 2007, pp. 3331-3334.
Shepherd, L. et al., "Towards direct biochemical analysis with weak inversion ISFETS", *Intl Workshop on Biomedical . . .* , 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, 5354-5361.
Simonian, A. L. et al., "FET based biosensors for the direct detection of organophosphate neurotoxins", *Electroanalysis*, vol. 16(22), 2004, pp. 1896-1906.
Souteyrand, E. et al., "Direct detection of the hybridization of synthetic homo-oligomer DNA sequences by field effect", *J Phys Chem B*, vol. 101(15), 1997, pp. 2980-2985.
Starodub, N. et al., "Immunosensor for the determination of the herbicide simazine based on an ion-selective field-effect transistor", *Analytica Chimica Acta*, vol. 424, 2000, pp. 37-43.
Takenaka, et al., "DNA Sensing on a DNA Probe-Modified Electrode Using Ferrocenylnaphthalene Dimide as the Electrochemically Active Ligand", *Anal. Chem.*, vol. 72, No. 6, 2000, 1334-1341.
Temes, G.C. et al., "A Tutorial Discussion of the Oversampling Method for A/D and D/A Conversion", *1990 IEEE International Symposium on Circuits and Systems*, vol. 2 of 4, 1990, 5 pages.
Thewes, R. et al., "CMOS-based Biosencor Arrays", *Proceedings of the Design, Automation and Test in Europe Conference and Exhibition*, 2005, 2 pages.
Tokuda, T. et al., "A CMOS image sensor with optical and potential dual imaging function for on-chip bioscientific applications", *Sensors and Actuators A*, vol. 125, No. 2, 2006, 273-280.
Tomaszewski, D. et al., "Electrical characterization of ISFETs", *J Telecomm Info Technol*, Mar. 2007, pp. 55-60.
Toumazou, C. et al., "Using transistors to linearase biochemistry" *Electronics Letters*, vol. 43(2), Jan. 18, 2007, 3 pages.
Truman, P., "Monitoring liquid transport and chemical composition in lab on . . .", *Lab on a Chip*, vol. 6, 2006, pp. 1220-1228.
Uslu, F. et al., "Labelfree fully electronic nucleic acid detection system based on a field-effect transistor device", *Biosens & Bioelectron*, vol. 19(12), 2004, pp. 1723-1731.
Van Der Schoot, Bart et al., "The Use of a Multi-ISFET Sensor Fabricated in a Single Substrate", *Letter to the Editors, Sensors and Actuators*, vol. 12, 1987, pp. 463-468.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.
Van Kerkhof, , "The Development of an ISFET based heparin sensor using the ion-step measuring method", *Biosensors and Bioelectronics*, vol. 9, Nos. 9-10, 1993, 463-472.
Van Kerkhof, , "The Development of an ISFET-based Heparin Sensor", *Thesis*, 1994.
Van Kerkhof, J et al., "The ISFET based heparin sensor with a monolayer of protamine as affinity ligand", *Biosensors & Bioelectronics*, vol. 10(3), 1995, pp. 269-282.
Van Kerkhof, J. et al., "ISFET Responses on a stepwise change in electrolyte concentration at constant pH", *Sensors Actuators B: Chemical*, vol. 18-19, 1994, pp. 56-59.

(56) References Cited

OTHER PUBLICATIONS

Vardalas, John, "Twists and Turns in the Development of the Transistor", *IEEE-USA Today's Engineer Online*, May 2003, 6 pages.
Voigt, H. et al., "Diamond-like carbon-gate pH-ISFET", *Sensors and Actuators B.*, vol. 44, 1997, pp. 441-445.
Wagner, T et al., "'All-in-one' solid-state device based on a light-addressable potentiometric sensor platform", *Sensors and Actuators B*, vol. 117, 2006, pp. 472-479.
Wang, W. et al., "Label-free detection of small-molecule-protein interactions by using nanowire nanosensors", *Proc. of the Natl. Acad.of Sciences (PNAS)*, vol. 102(9), 2005, 3208-3212.
Wilhelm, D. et al., "PH Sensor Based on Differential Measurements on One pH-FET Chip", *Sensors and Actuators B*, vol. 4, 1991, pp. 145-149.
Woias, P , "Modelling the short time response of ISFET sensors", *Sensors and Actuators B*, vol. 24-25, 1995, pp. 211-217 .
Woias, P. et al., "Slow pH response effects of silicon nitride ISFET sensors", *Sensors and Actuators B*, vol. 48, 1998, pp. 501-504.
Wood, et al., "Base composition-independent hybridization in tetramethylammonium chloride: a method for oligonucleotide screening of highly complex gene libraries", *Proceedings of the National Academy of Sciences*, vol. 82, 1985, 1585-1588 .
Wu, P. et al., "DNA and protein microarray printing on silicon nitride waveguide surfaces", *Biosensens Bioelectron*, vol. 21(7), 2006, pp. 1252-1263.
Xu, J-J et al., "Analytical Aspects of FET-Based Biosensors", *Frontiers in Bioscience*, vol. 10, 2005, pp. 420-430 .
Yeow, T.C.W. et al., "A very large integrated pH-ISFET sensor array chip compatible with standard CMOS processes", *Sensor and Actuators B*, vol. 44, 1997, 434-440.
Yoshida, Shoji et al., "Development of a Wide Range pH Sensor based on Electrolyte-Insulator-Semiconductor Structure with Corrosion-Resistant Al2O3—Ta2O5 and Al2O3—ZrO2", *Journal of the Electrochemical Society* vol. 151(3), 2004, pp. H53-H58.
Yuqing, M. et al., "Ion sensitive field effect trnasducer-based biosensors", *Biotechnology Advances*, vol. 21, 2003, pp. 527-534 .
Zhang, X. et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, pp. v-viii.
Zhao, B. et al., "Floating-Gate Ion Sensitive Field-Effect Transistor for Chemical and Biological Sensing", *MRS Proceedings*, vol. 828, 2005, pp. 349-354.
Zhou, et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, 1-11
"OV5640 Datasheet Product Specification", *1/4 color CMOS QSXGA (5 megapixel) image sensor with OmniBSI technology*, May 1, 2011, p. 1, line 9 and pp. 2-7, paragraph 1.
Liu, Yan et al., "An ISFET based sensing array with sensor offset compensation and pH sensitivity enhancement", *Proc. of 2010 IEEE Int. Symp. on Circuits and Systems (ISCAS)*, ISBN:978-1-4244-5308-5, Jun. 2, 2010, pp. 2283-2286.
Morgenshtein, Arkadiy et al., "Wheatstone-Bridge readout interface for ISFET/REFET applications", *Sensors and Actuators B: Chemical*, vol. 98, No. 1, Mar. 2004, pp. 18-27.
Nakazato, Kazuro, "An Integrated ISFET Sensor Array", *Sensors*, Nov. 2009, vol. 9, No. 11, ISSN:1424-8220, [online], Internet, URL, http://www.mdpi.com/1424-8220/9/11/8831/pdf, Nov. 2009, pp. 8831-8851.
PCT/US2015/066023, "International Search Report and Written Opinion of the International Searching Authority" mailed Mar. 14, 2016, 18 pages.
PCT/US2015/066052, "International Search Report and Written Opinion of the International Searching Authority" mailed Apr. 7, 2016, 19 pages.
Schroder, Dieter K., "6. Oxide and Interface Trapped Charges, Oxide Thickness", *Semiconductor Material and Device Characterization, John Wiley & Sons*, ISBN: 978-0-471-73906-7, Feb. 17, 2006, pp. 319-387.
Nakazato, Kazuo, "An Integrated ISFET Sensor Array", *Sensors*, vol. 9, No. 11, 2009, pp. 8831-8851.
Wen-Yaw, Chung A. et al., "New ISFET interface circuit design with temperature Compensation", *CiteSeerx*—URL:http://citeseerx.ist.psu.edu/viewdoc/download?doi=10.1.1.95.2321&rep=rep1&type=pdf, 2006, 1.
Izuru, "Kojien", *published by Owanami, Fourth Edition*, with English Translation, 1991, 2683.
Moriizumi, "Biosensors", *Oyo Buturi (monthly publication of the Japan Society of Applied Physics)*, vol. 54, No. 2, Feb. 10, 1985, pp. 98-114.
Nakazato et al., "28p-Y-7 ISFET sensor array integrated circuits based on standard CMOS process", *The 55th annual meeting of the Japan Society of Applied Physics, book of Abstracts*, ISBN:978-4-903968-44-5, Mar. 27, 2008, p. 70.

\* cited by examiner

CHEMICAL DEVICE WITH THIN CONDUCTIVE ELEMENT

CROSS-REFERENCE TO RELATED APPLICATIONS

This application is a continuation of U.S. patent application Ser. No. 14/198,402 filed Mar. 5, 2014, which claims priority to U.S. Provisional Application No. 61/868,942 filed Aug. 22, 2013 and 61/790,866 filed Mar. 15, 2013, the entire contents of which are incorporated by reference herein in their entirety.

FIELD OF THE INVENTION

This disclosure, in general, relates to sensors for chemical analysis, and to methods for manufacturing such sensors.

BACKGROUND

A variety of types of chemical devices have been used in the detection of chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect and/or determine characteristics of the chemical reaction. The threshold voltage may, for example, be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, due to the protonation or deprotonation of surface charge groups caused by the ions present in the analyte solution. The change in surface potential at the sensitive area of the ISFET affects the threshold voltage of the device, which can be measured to indicate the presence and/or concentration of ions within the solution. Arrays of ISFETs may be used for monitoring chemical reactions, such as DNA sequencing reactions, based on the detection of ions present, generated, or used during the reactions. See, for example, U.S. Pat. No. 7,948, 015 to Rothberg et al., which is incorporated by reference herein in its entirety. More generally, large arrays of chemFETs or other types of chemical devices may be employed to detect and measure static and/or dynamic amounts or concentrations of a variety of analytes (e.g. hydrogen ions, other ions, compounds, etc.) in a variety of processes. The processes may, for example, be biological or chemical reactions, cell or tissue cultures or monitoring neural activity, nucleic acid sequencing, etc.

An issue that arises in the operation of large scale chemical device arrays is the susceptibility of the sensor output signals to noise. Specifically, the noise affects the accuracy of the downstream signal processing used to determine the characteristics of the chemical and/or biological process being detected by the sensors. It is therefore desirable to provide devices including low noise chemical devices, and methods for manufacturing such devices.

SUMMARY

In one exemplary embodiment, a chemical device is disclosed. The sensor includes a chemically-sensitive field effect transistor including a floating gate structure comprising a plurality of floating gate conductors electrically coupled to one another. A conductive element overlies and is in communication with an uppermost floating gate conductor in the plurality of floating gate conductors. The conductive element may be wider and thinner than the uppermost floating gate conductor. The sensor further includes a dielectric material defining an opening extending to an upper surface of the conductive element. Accordingly to an exemplary embodiment, the conductive element may comprise at least one of titanium, tantalum, titanium nitride, and aluminum, and/or oxides and/or mixtures thereof. According to another embodiment, the distance between adjacent conductive elements in the chemical device is about 0.18 microns. In yet another embodiment, the thickness of the conductive element is about 0.1-0.2 microns. In one embodiment, the uppermost floating gate conductor in the plurality of floating gate conductors may have a thickness greater than a thickness of other floating gate conductors in the plurality of floating gate conductors. In another embodiment, the conductive element may comprise a material different from a material comprising the uppermost floating gate conductor. Accordingly to an exemplary embodiment, the conductive element may comprise a material different from a material comprising the uppermost floating gate conductor. According to another embodiment, an inner surface of the dielectric material and the upper surface of the conductive element define an outer surface of a reaction region for the chemical device. In yet another embodiment, the plurality of floating gate conductors is within layers that further include array lines and bus lines. In one embodiment, the chemical devices includes a sensor region containing the chemically-sensitive field effect transistor and a peripheral region containing peripheral circuitry to obtain a signal from the chemically-sensitive field effect transistor. In one embodiment, the conductive element is within a conductive layer that is only within the sensor region. In another embodiment, the conductive element comprises a material not within the peripheral region. Accordingly to an exemplary embodiment, the chemically-sensitive field effect transistor may include a floating gate structure comprising a plurality of conductors electrically coupled to one another and separated by dielectric layers, and the floating gate conductor may be an uppermost conductor in the plurality of conductors. According to another embodiment, a first layer of the dielectric material may be silicon nitride and a second layer may be at least one of silicon dioxide and tetraethyl orthosilicate, and the second layer defines sidewalls of the opening. In one embodiment, the chemical device may further comprise a microfluidic structure in fluid flow communication with the chemically-sensitive field effect transistor, and arranged to deliver analytes for sequencing.

In another exemplary embodiment, method for manufacturing a chemical device is disclosed. The method includes forming a chemically-sensitive field effect transistor including a floating gate structure comprising a plurality of floating gate conductors electrically coupled to one another. The method further includes forming a conductive element overlying and in communication with an uppermost floating gate conductor in the plurality of floating gate conductors. The conductive element is wider and thinner than the uppermost floating gate conductor. The method further includes forming a dielectric material defining an opening extending to an upper surface of the conductive element. Accordingly to an exemplary embodiment, the upper surface of the conductive element defines a bottom surface of a reaction region for the chemical sensor. According to another embodiment, an inner surface of the dielectric material and the upper surface of the conductive element define an outer boundary of a reaction region for the chemical sensor. In yet another embodiment, the conductive element is formed within a conductive layer that is only within a sensor region of the chemical device.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

Figure 1:
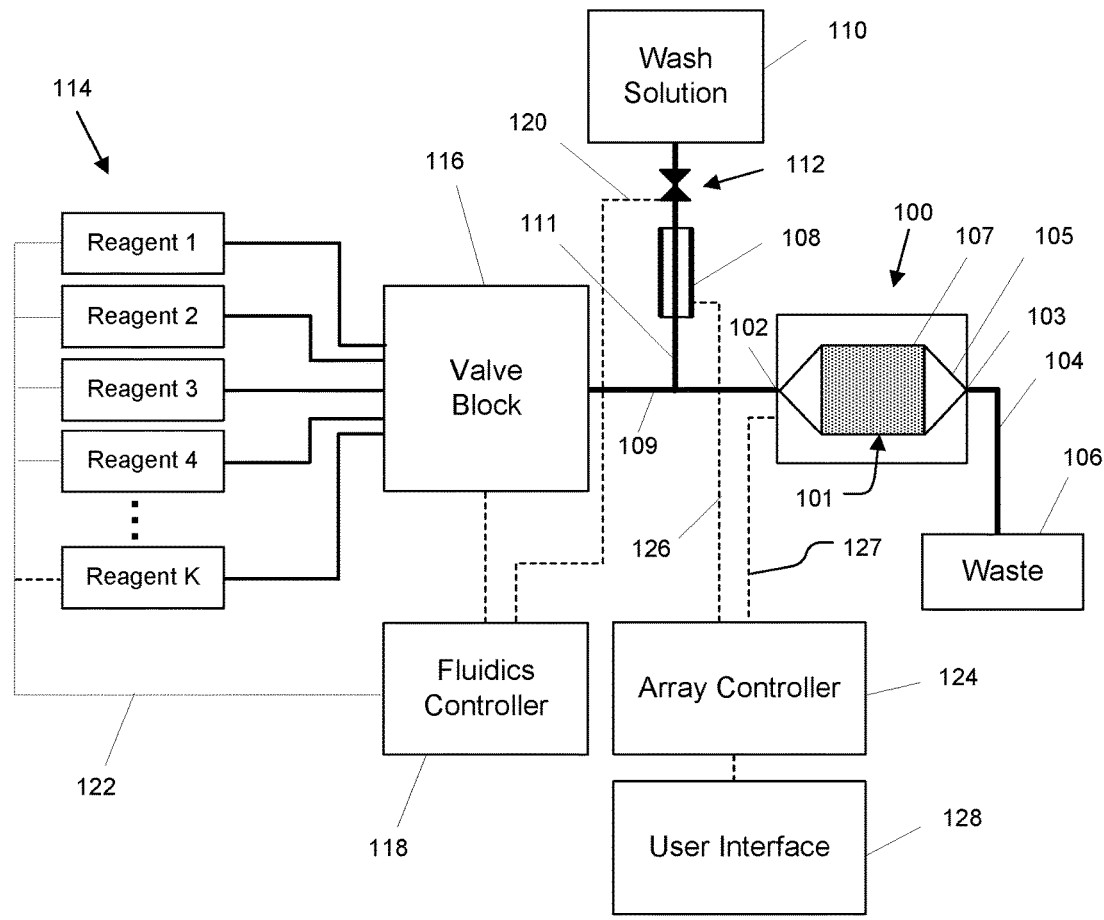
FIG. 1 illustrates a block diagram of components of a system for nucleic acid sequencing according to an exemplary embodiment.

Chemical devices are described that include low noise chemical devices, such as chemically-sensitive field effect transistors (chemFETs), for detecting chemical reactions within overlying, operationally associated reaction regions. A sensor of a chemical device may comprise a plurality of floating gate conductors with a sensing layer deposited on an uppermost floating conductor of the plurality of floating gate conductors. However, Applicants have found that adding an additional layer above uppermost floating conductor of the plurality of floating gate conductors that is dedicated to sensing has advantages that overcome the technical challenges and cost of the additional layer. For example, Applicants have found that advantages in the chemical devices described herein include providing enhanced lithographic process margin; (for example, prevent misalign of openings and/or burnout); and providing larger openings in the dielectric than would be possible were the sensing area directly on top of the uppermost floating gate conductor (for example, larger openings can accommodate more signal).

Exemplary chemical devices described herein have sensing surface areas which may comprise a dedicated layer for sensing. In embodiments described herein, a conductive element overlies and is in communication with an uppermost floating gate conductor. Because the uppermost floating gate conductor may be used to provide array lines (e.g. word lines, bit lines, etc.) and bus lines for accessing/powering the chemical devices, the uppermost floating gate conductor should be a suitable material or mixture of materials and of sufficient thickness therefor. Since the conductive element is within a different layer on the substrate of the chemical device, the conductive element may function as a dedicated sensing surface area independent of the material and thickness of the uppermost floating gate structure. For example, the conductive element may be wider than the uppermost floating gate conductor such that the sensing surface area can be relatively large. For example, the conductive element may be thinner than the uppermost floating gate conductor such that the sensing surface area can provide increased sensitivity for sensing. As a result, low noise chemical devices can be provided in a high density array, such that the characteristics of reactions can be accurately detected.

Additionally, the uppermost floating gate conductor does not need to be pushed to process limits; while adjacent floating gate conductors should have a thickness (i.e. for low resistivity) suitable for carrying high currents, the space between adjacent floating gate conductors does not need to be the minimum space allowed by process design rules. The material(s) used for the uppermost floating gate conductor should be suitable for high currents. Providing the conductive element overlying and in communication with the uppermost floating gate conductor provides greater freedom in choice of material for the conductive element since the conductive element is on a different layer than the uppermost floating gate conductor.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical devices as described herein. The flow cell 101 includes an inlet 102, an outlet 103, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, or other suitable methods, and may be discarded into the waste container 106 after exiting the outlet 103 of the flow cell 101. The fluidics controller 118 may control driving forces for the reagents 114 and the operation of valve 112 and valve block 116 with suitable software. The microwell array 107 includes an array of reaction regions as described herein, also referred to herein as microwells, which are operationally associated with corresponding chemical devices in the sensor array. For example, each reaction region may be coupled to a chemical device suitable for detecting an analyte or reaction property of interest within that reaction region. The microwell array 107 may be integrated in the integrated circuit device 100, so that the microwell array 107 and the sensor array are part of a single device or chip. The flow cell 101 may have a variety of configurations for controlling the path and flow rate of reagents 114 over the microwell array 107. The array controller 124 provides bias voltages and timing and control signals to the integrated circuit device 100 for reading the chemical devices of the sensor array. The array controller 124 also provides a reference bias voltage to the reference electrode 108 to bias the reagents 114 flowing over the microwell array 107.

During an experiment, the array controller 124 collects and processes output signals from the chemical devices of the sensor array through output ports on the integrated circuit device 100 via bus 127. The array controller 124 may be a computer or other computing means. The array controller 124 may include memory for storage of data and software applications, a processor for accessing data and executing applications, and components that facilitate communication with the various components of the system in FIG. 1. The values of the output signals of the chemical devices indicate physical and/or chemical parameters of one or more reactions taking place in the corresponding reaction regions in the microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety. The user interface 128 may display information about the flow cell 101 and the output signals received from chemical devices in the sensor array on the integrated circuit device 100. The user interface 128 may also display instrument settings and controls, and allow a user to enter or set instrument settings and controls.

In an exemplary embodiment, during the experiment the fluidics controller 118 may control delivery of the individual reagents 114 to the flow cell 101 and integrated circuit device 100 in a predetermined sequence, for predetermined durations, at predetermined flow rates. The array controller 124 can collect and analyze the output signals of the chemical devices indicating chemical reactions occurring in response to the delivery of the reagents 114. During the experiment, the system may also monitor and control the temperature of the integrated circuit device 100, so that reactions take place and measurements are made at a known predetermined temperature. The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figure 2:
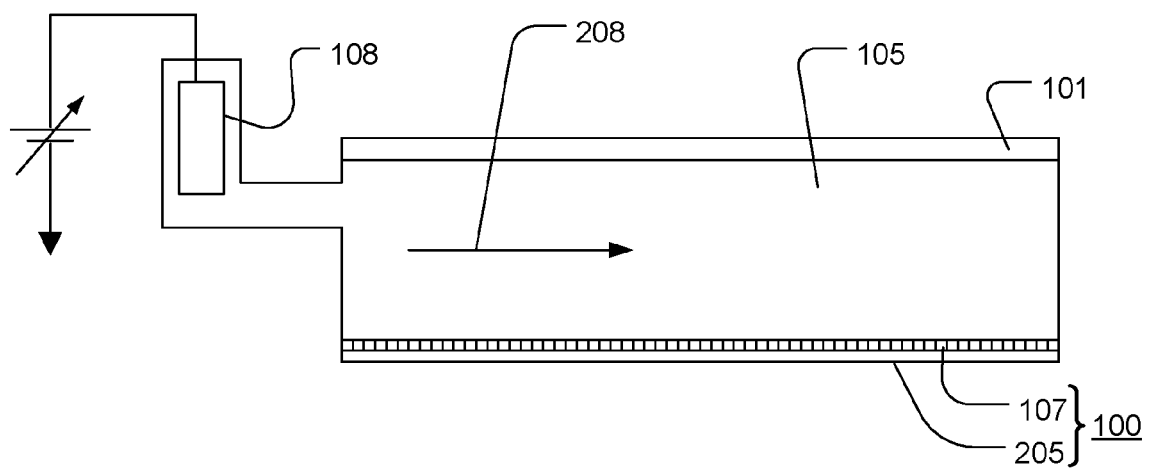
FIG. 2 illustrates a cross-sectional view of a portion of the integrated circuit device and flow cell according to an exemplary embodiment.

FIG. 2 illustrates a cross-sectional view of a portion of the integrated circuit device 100 and flow cell 101. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed. The chemical devices of the sensor array 205 are responsive to (and generate output signals) chemical reactions within associated reaction regions in the microwell array 107 to detect an analyte or reaction property of interest. The chemical devices of the sensor array 205 may, for example, be chemically sensitive field-effect transistors (chemFETs), such as ion-sensitive field effect transistors (ISFETs). Examples of chemical devices and array configurations that may be used in embodiments are described in U.S. Patent Application Publication No. 2010/0300559, No. 2010/0197507, No. 2010/0301398, No. 2010/0300895, No. 2010/01307a43, and No. 2009/0026082, and U.S. Pat. No. 7,575,865, each of which are incorporated by reference herein in their entirety.

Figure 3:
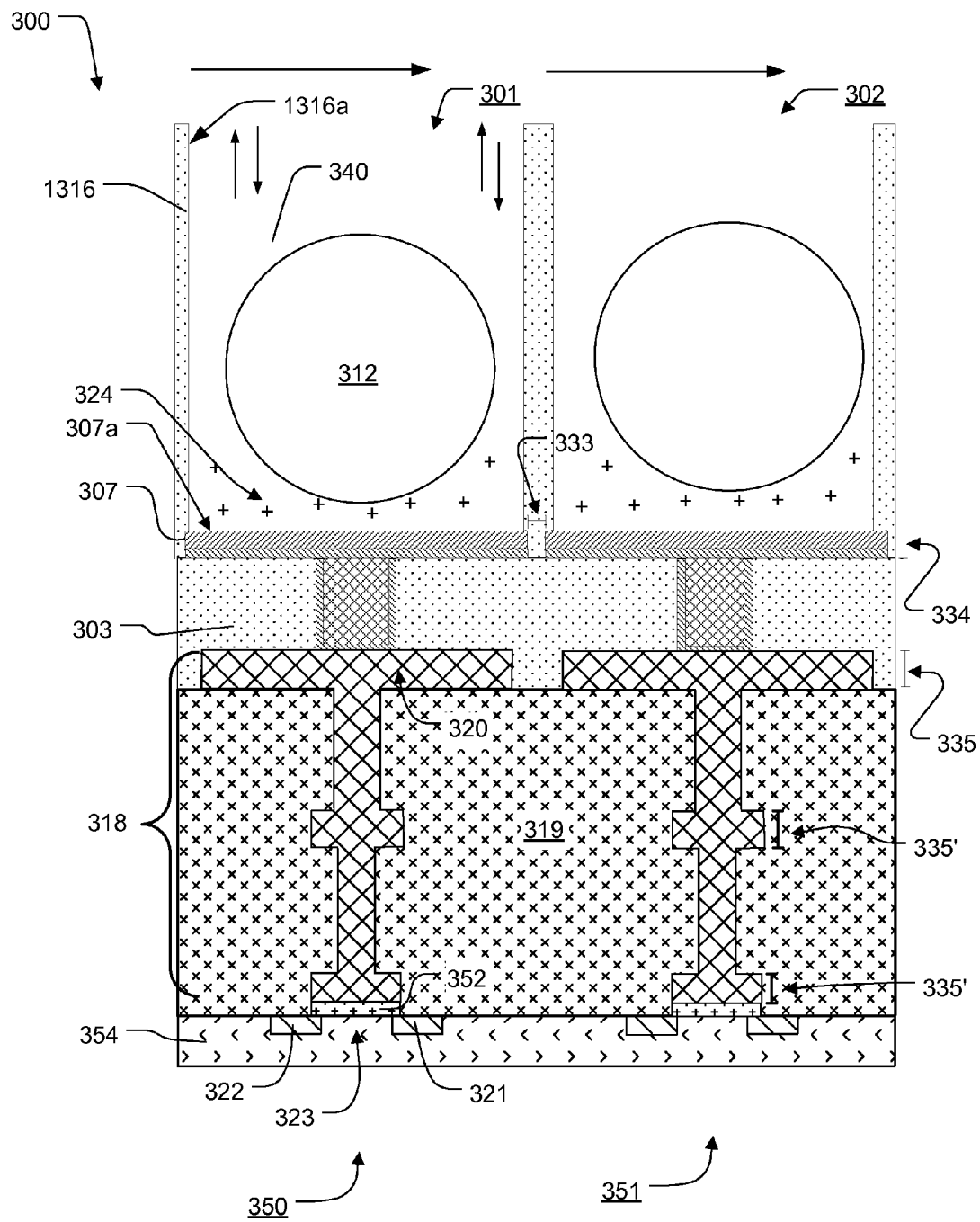
FIG. 3 illustrates cross-sectional of representative chemical devices and corresponding reaction regions according to an exemplary embodiment.

FIG. 3 illustrates a cross-sectional view of two representative chemical devices and their corresponding reaction regions according to an exemplary embodiment. In FIG. 3, two chemical devices 350, 351 are shown, representing a small portion of a sensor array that can include millions of chemical devices. Chemical device 350 is coupled to corresponding reaction region 301, and chemical device 351 is coupled to corresponding reaction region 302. Chemical device 350 is representative of the chemical devices in the sensor array. In the illustrated example, the chemical device 350 is a chemically-sensitive field effect transistor (chemFET), more specifically an ion-sensitive field effect transistor (ISFET) in this example. The chemical device 350 includes a floating gate structure 318 having a sensor plate 320 coupled to the reaction region 301 by a conductive element 307. As is illustrated in FIG. 3, the sensor plate 320 is the uppermost floating gate conductor in the floating gate structure 318. In the illustrated example, the floating gate structure 318 includes multiple patterned layers of conductive material within layers of dielectric material 319. The chemical device 350 also includes a source region 321 and a drain region 322 within a semiconductor substrate 354. The source region 321 and the drain region 322 comprise doped semiconductor material having a conductivity type different from the conductivity type of the substrate 354. For example, the source region 321 and the drain region 322 may comprise doped P-type semiconductor material, and the substrate may comprise doped N-type semiconductor material. Channel region 323 separates the source region 321 and the drain region 322. The floating gate structure 318 overlies the channel region 323, and is separated from the substrate 354 by a gate dielectric 352. The gate dielectric 352 may be silicon dioxide, for example. Alternatively, other dielectrics may be used for the gate dielectric 352.

As shown in FIG. 3, the dielectric material defines the reaction region 301 which may be within opening defined by an absence of dielectric material. The dielectric material 303 may comprise one or more layers of material, such as silicon dioxide or silicon nitride or any other suitable material or mixture of materials. The dimensions of the openings, and their pitch, can vary from implementation to implementation. In some embodiments, the openings can have a characteristic diameter, defined as the square root of 4 times the plan view cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or not greater than 0.1 micrometers.

The chemical device 350 includes a conductive element 307 overlying and in communication with an uppermost floating gate conductor in the plurality of floating gate conductors. The conductive element is wider and thinner than the uppermost floating gate conductor, as illustrated in FIG. 3. In the illustrated embodiment, the dielectric material defines an opening extending to an upper surface of the conductive element. The upper surface 307a of the conductive element 307 defines a bottom surface of a reaction region for the chemical device. Viewed another way, the upper surface 307a of the conductive element 307 and a lower portion of an inner surface 1316a of the dielectric material 1316 define a bottom region of a reaction region for the chemical device. The conductive element 307 may have a width W wider than a width W' of the reaction region. According to one embodiment, the distance 333 between adjacent conductive elements in the chemical device is about 0.18 microns. According to another embodiment, the thickness 334 of the conductive element is about 0.1-0.2 microns. In one embodiment, the uppermost floating gate conductor in the plurality of floating gate conductors may have a thickness 335 greater than a thickness 335' of other floating gate conductors in the plurality of floating gate conductors. In another embodiment, the conductive element 370 may comprise a material different from a material comprising the uppermost floating gate conductor.

The upper surface 307a of the conductive element 307 acts as the sensing surface for the chemical device 350. The conductive element as discussed throughout the disclosure may be formed in various shapes (width, height, etc.) depending on the materials/etch techniques/fabrication processes etc. used during the manufacture process. The conductive element 307 may comprise one or more of a variety of different materials to facilitate sensitivity to particular ions (e.g. hydrogen ions). Accordingly to an exemplary embodiment, the conductive element may comprise at least one of titanium, tantalum, titanium nitride, and aluminum, and/or oxides and/or mixtures thereof. The conductive element 307 allows the chemical device 350 to have a sufficiently large surface area to avoid the noise issues associated with small sensing surfaces. The plan view area of the chemical device is determined in part by the width (or diameter) of the reaction region 301 and can be made small, allowing for a high density array. In addition, because the reaction region 301 is defined by upper surface 307a of the conductive element 307 and an inner surface 1316a of the dielectric material 1316, the sensing surface area depends upon the depth and the circumference of the reaction region 301, and can be relatively large. As a result, low noise chemical devices 350, 351 can be provided in a high density array, such that the characteristics of reactions can be accurately detected.

During manufacturing and/or operation of the device, a thin oxide of the material of the conductive element 307 may be grown on the upper surface 307a which acts as a sensing material (e.g. an ion-sensitive sensing material) for the chemical device 350. For example, in one embodiment the electrically conductive element may be titanium nitride, and titanium oxide or titanium oxynitride may be grown on the upper surface 307a during manufacturing and/or during exposure to solutions during use. Whether an oxide is formed depends on the conductive material, the manufacturing processes performed, and the conditions under which the device is operated. In the illustrated example, the conductive element 307 is shown as a single layer of material. More generally, the electrically conductive element may comprise one or more layers of a variety of electrically conductive materials, such as metals or ceramics, or any other suitable conductive material or mixture of materials, depending upon the implementation. The conductive material can be, for example, a metallic material or alloy thereof, or can be a ceramic material, or a combination thereof. An exemplary metallic material includes one of aluminum, copper, nickel, titanium, silver, gold, platinum, hafnium, lanthanum, tantalum, tungsten, iridium, zirconium, palladium, or a combination thereof. An exemplary ceramic material includes one of titanium nitride, titanium aluminum nitride, titanium oxynitride, tantalum nitride, or a combination thereof. In some alternative embodiments, an additional conformal sensing material (not shown) is deposited on the upper surface 307a of the conductive element 307. The sensing material may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the implementation.

Referring again to FIG. 3, in operation, reactants, wash solutions, and other reagents may move in and out of the reaction region 301 by a diffusion mechanism 340. The chemical device 350 is responsive to (and generates an output signal related to) the amount of a charge 324 proximate to the conductive element 307. The presence of charge 324 in an analyte solution alters the surface potential at the interface between the analyte solution and the upper surface 307a of the conductive element 307, due to the protonation or deprotonation of surface charge groups caused by the ions present in the analyte solution. Changes in the charge 324 cause changes in the voltage on the floating gate structure 318, which in turn changes in the threshold voltage of the transistor of the chemical device 350. This change in threshold voltage can be measured by measuring the current in the channel region 323 between the source region 321 and a drain region 322. As a result, the chemical device 350 can be used directly to provide a current-based output signal on an array line connected to the source region 321 or drain region 322, or indirectly with additional circuitry to provide a voltage-based output signal.

As described in more detail below with respect to FIGS. 4-14, the conductive element 307 is overlying and in communication with an uppermost floating gate conductor 320. The conductive element is wider and thinner than the uppermost floating gate conductor. Because the charge 324 may be more highly concentrated near the bottom of the reaction region 301, in some embodiments variations in the dimensions of the conductive element may have a significant effect on the amplitude of the signal detected in response to the charge 324. In an embodiment, reactions carried out in the reaction region 301 can be analytical reactions to identify or determine characteristics or properties of an analyte of interest. Such reactions can generate directly or indirectly byproducts that affect the amount of charge adjacent to the conductive element 307. If such byproducts are produced in small amounts or rapidly decay or react with other constituents, multiple copies of the same analyte may be analyzed in the reaction region 301 at the same time in order to increase the output signal generated. In an embodiment, multiple copies of an analyte may be attached to a solid phase support 312, either before or after deposition into the reaction region 301. The solid phase support 312 may be microparticles, nanoparticles, beads, solid or porous comprising gels, or the like. For simplicity and ease of explanation, solid phase support 312 is also referred herein as a particle. The solid phase support may be of varied size, as would be understood by one of ordinary skill in the art. Further, the solid support may be positioned in the opening at various places. For a nucleic acid analyte, multiple, connected copies may be made by rolling circle amplification (RCA), exponential RCA, polymerase chain reaction (PCR) or like techniques, to produce an amplicon without the need of a solid support.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals of the chemical devices indicative of ion concentration during each nucleotide flow, the identity of the type, sequence and number of nucleotide(s) associated with a sample nucleic acid present in a reaction region coupled to a chemical device can be determined.

Figure 4:
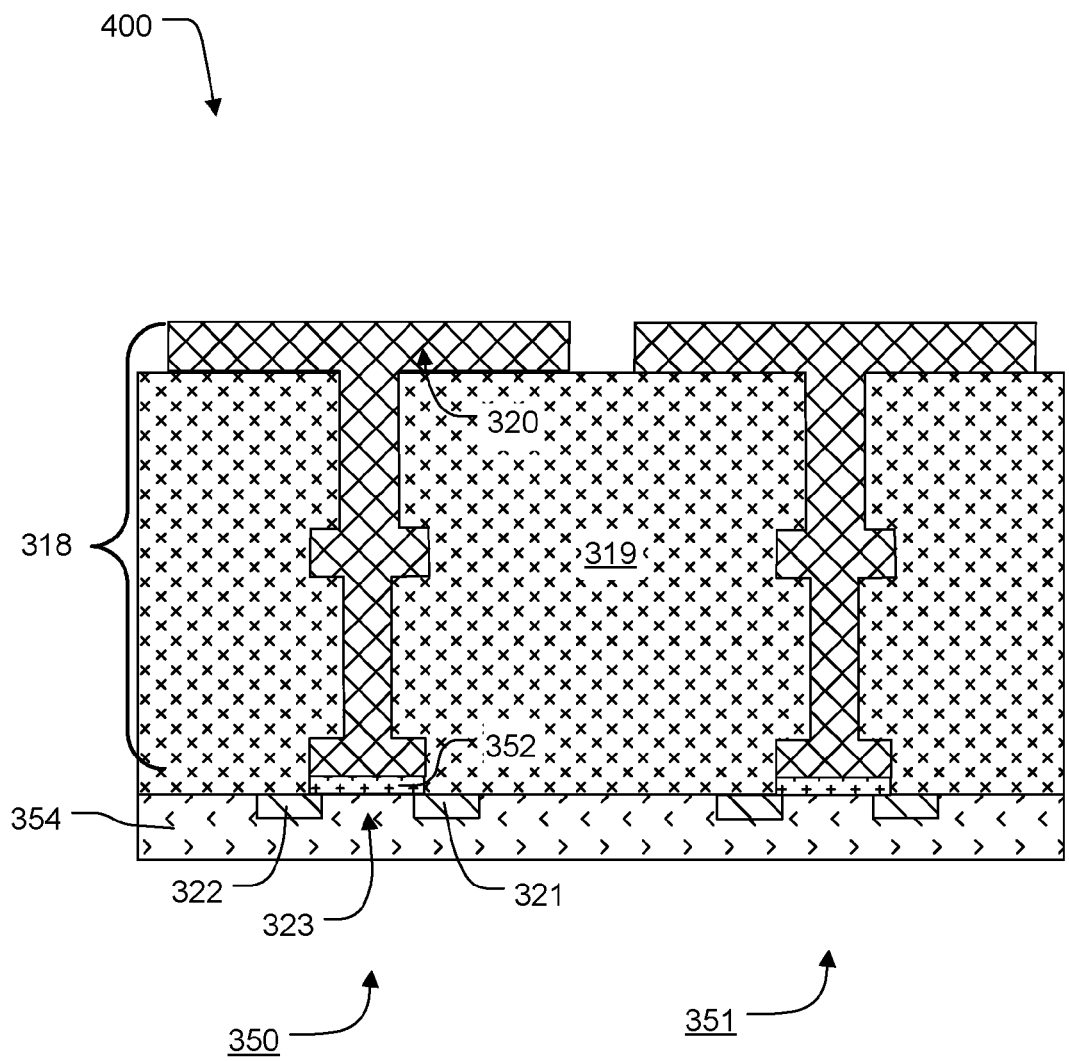
FIGS. 4 to 14 illustrate stages in a manufacturing process for forming an array of chemical devices and corresponding well structures according to an exemplary embodiment.

FIGS. 4-14 illustrate stages in a manufacturing process for forming an array of chemical devices and corresponding well structures according to an exemplary embodiment. FIG. 4 illustrates a structure 400 including the floating gate structures (e.g. floating gate structure 318) for the chemical devices 350, 351. The structure 400 can be formed by depositing a layer of gate dielectric material on the semiconductor substrate 354, and depositing a layer of polysilicon (or other electrically conductive material) on the layer of gate dielectric material. The layer of polysilicon and the layer gate dielectric material can then be etched using an etch mask to form the gate dielectric elements (e.g. gate dielectric 352) and the lowermost conductive material element of the floating gate structures. Following formation of an ion-implantation mask, ion implantation can then be performed to form the source and drain regions (e.g. source region 321 and a drain region 322) of the chemical devices. A first layer of the dielectric material 319 can be deposited over the lowermost conductive material elements. Conductive plugs can then be formed within vias etched in the first layer of dielectric material 319 to contact the lowermost conductive material elements of the floating gate structures. A layer of conductive material can then be deposited on the first layer of the dielectric material 319 and patterned to form second conductive material elements electrically connected to the conductive plugs. This process can then be repeated multiple times to form the completed floating gate structure 318 shown in FIG. 4. Alternatively, other and/or additional techniques may be performed to form the structure. Forming the structure 400 in FIG. 4 can also include forming additional elements such as array lines (e.g. word lines, bit lines, etc.) for accessing the chemical devices, additional doped regions in the substrate 354, and other circuitry (e.g. access circuitry, bias circuitry etc.) used to operate the chemical devices, depending upon the device and array configuration in which the chemical devices described herein are implemented. In some embodiments, the elements of the structure may, for example, be manufactured using techniques described in U.S. Patent Application Publication No. 2010/0300559, No. 2010/0197507, No. 2010/0301398, No. 2010/0300895, No. 2010/013071a43, and No. 2009/0026082, and U.S. Pat. No. 7,575,865, each of which were incorporated by reference in their entirety above.

Figure 5:
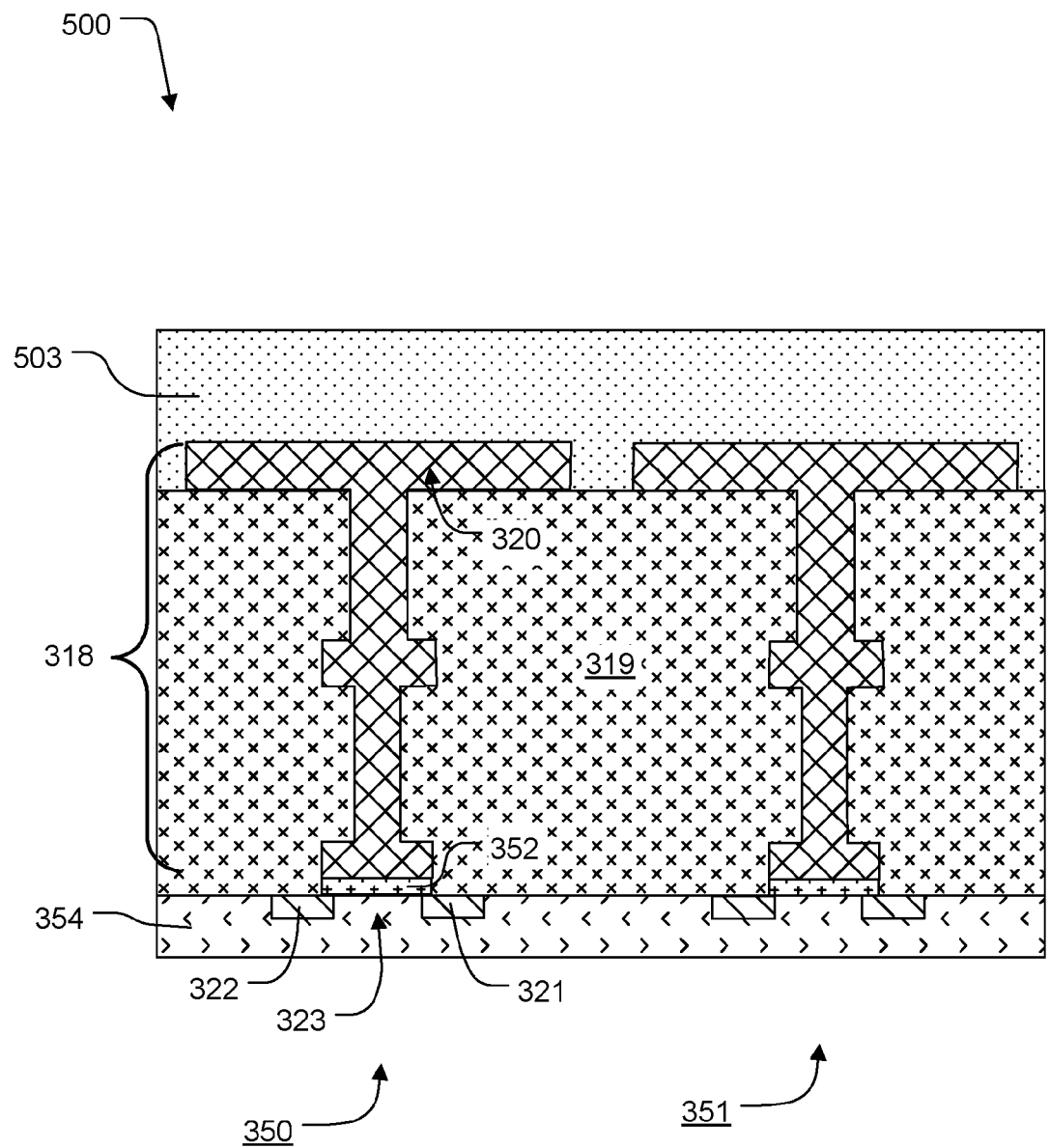
Figure 6:
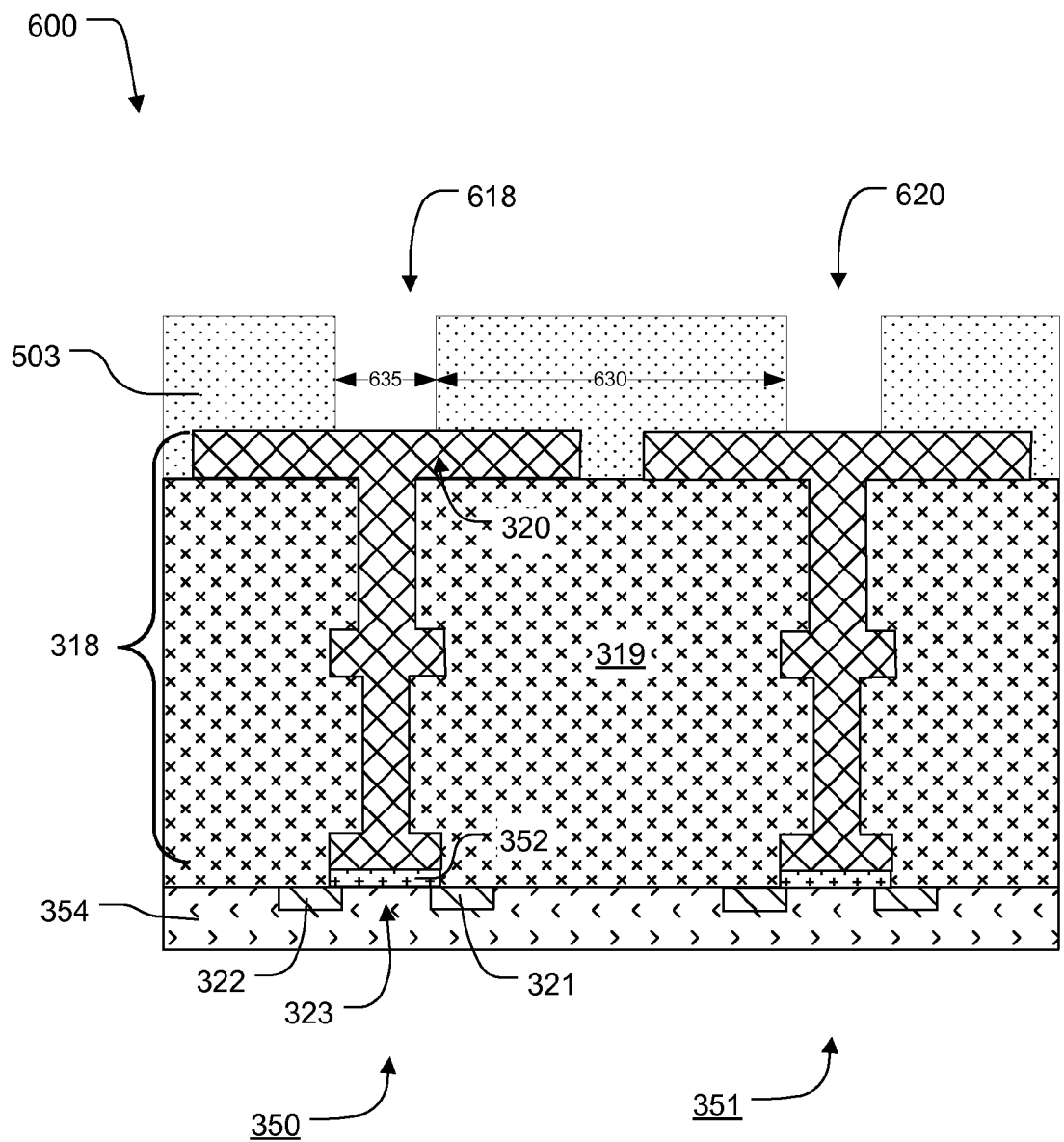

As illustrated in the structure 500 illustrated in FIG. 5, a dielectric material 503 may be formed on the sensor plate 320 of the field effect transistor of the chemical device 350. Next, as illustrated in FIG. 6, the dielectric material 503 of the structure 500 in FIG. 5 is etched to form openings 618, 620 (for vias) extending to the upper surfaces of the floating gate structures of the chemical devices 350, 351, resulting in the structure 600 illustrated in FIG. 6. The openings 618, 620 may, for example, be formed by using a lithographic process to pattern a layer of photoresist on the dielectric material 503 to define the locations of the openings 618, 620, and then anisotropically etching the dielectric material 503 using the patterned photoresist as an etch mask. The anisotropic etching of the dielectric material 503 may, for example, be a dry etch process, such as a fluorine based Reactive Ion Etching (RIE) process. In the illustrated embodiment, the openings 618, 620 are separated by a distance 630 and the openings 618, 620 are of a suitable dimension for a via. For example, the separation distance 630 may be a minimum feature size for the process (e.g. a lithographic process) used to form the openings 618, 620. In such a case, the distance 630 may be significantly more than the width 635. Next, a layer of conductive material 704 is deposited on the structure 600 illustrated in FIG. 6, resulting in the structure 700 illustrated in FIG. 7. Conductive material 704 may be referred to as a conductive liner. The conductive material 704 may comprise one or more layers of electrically conductive material. For example, the conductive material 704 may be a layer of titanium nitride, or a layer of titanium. Alternatively, other and/or additional conductive materials may be used, such as those described above with reference to the electrically conductive element. In addition, more than one layer of conductive material may be deposited. The conductive material 704 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc.

Figure 7:
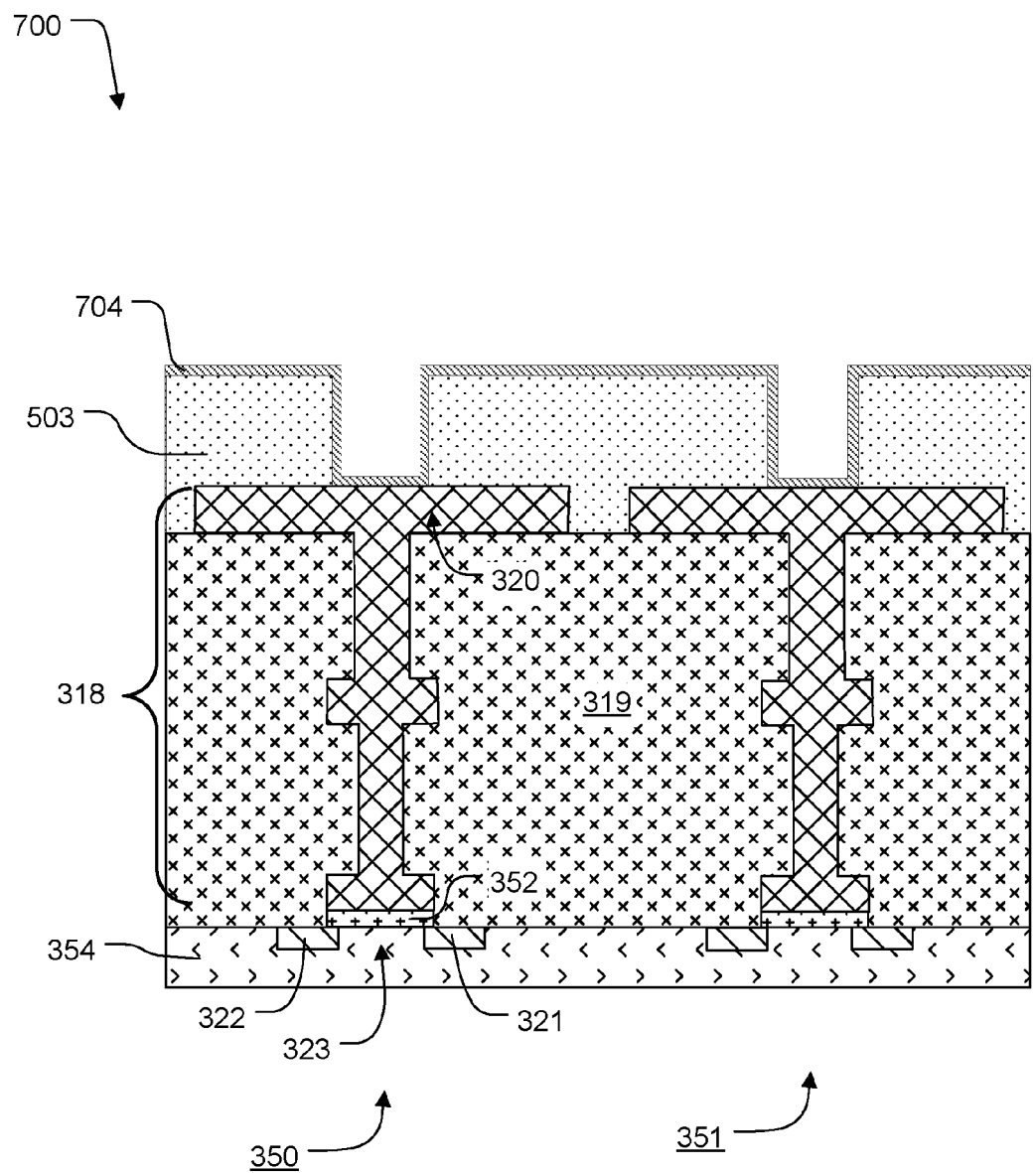
Figure 8:
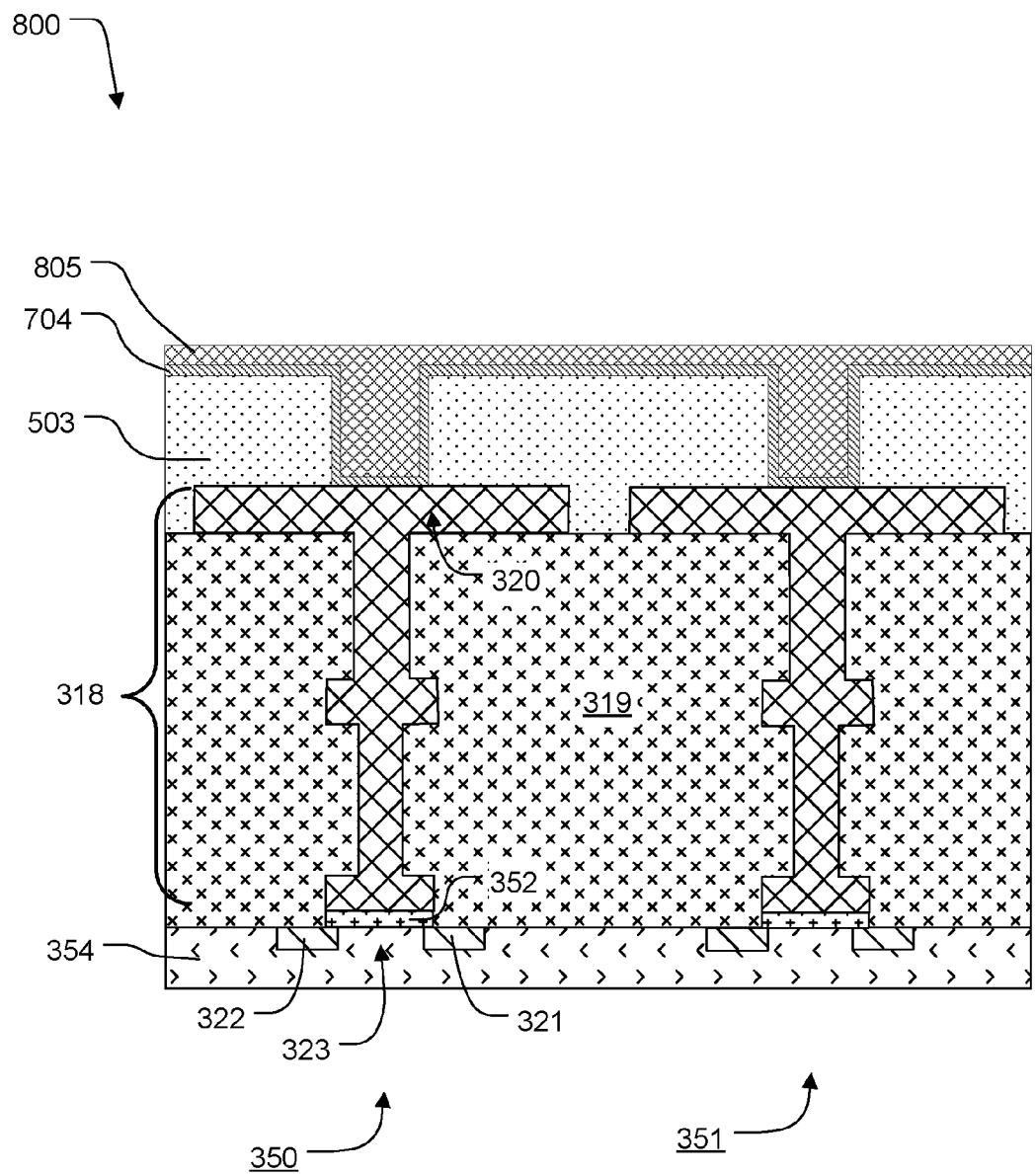
Figure 9:
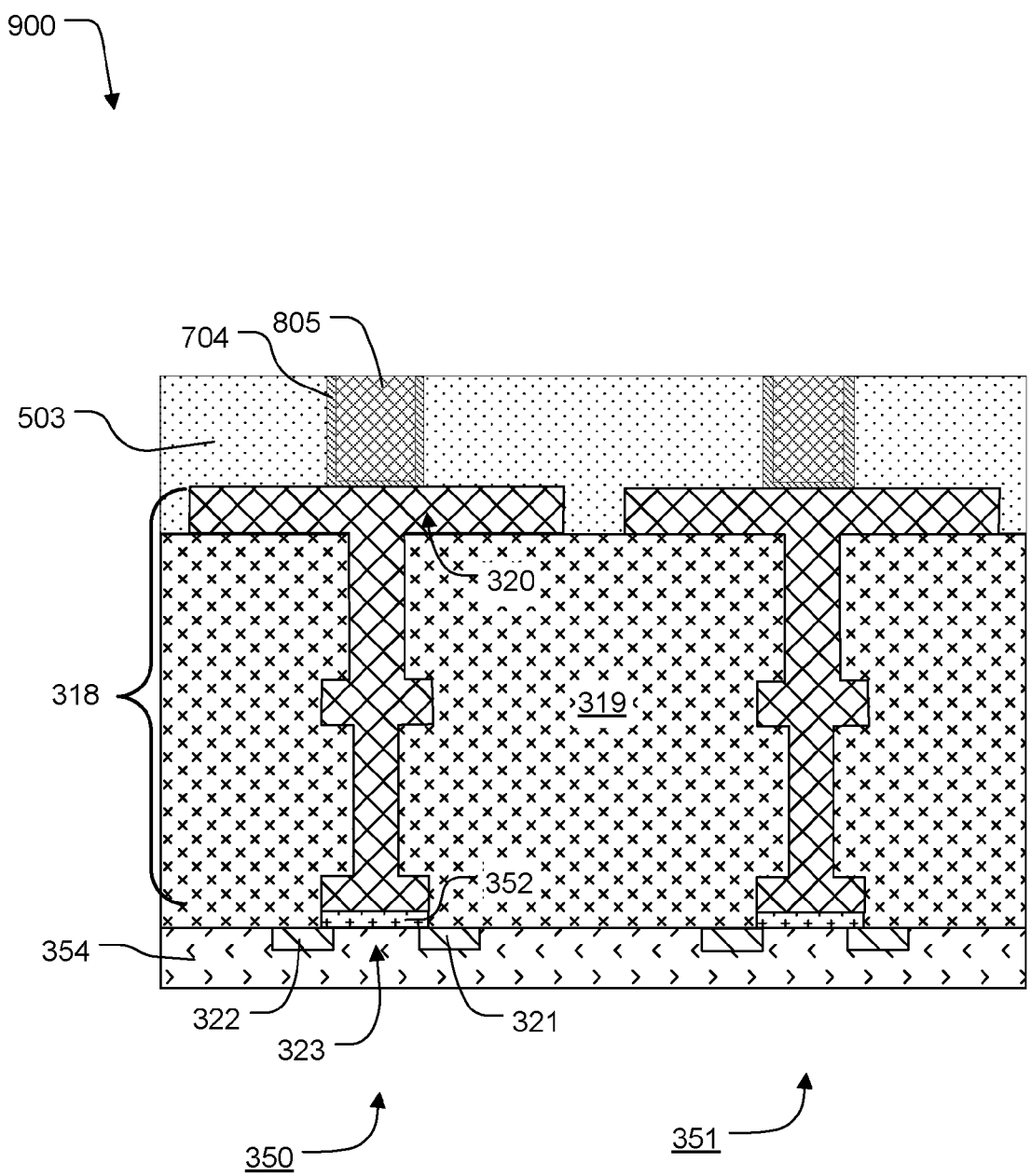
Figure 10:
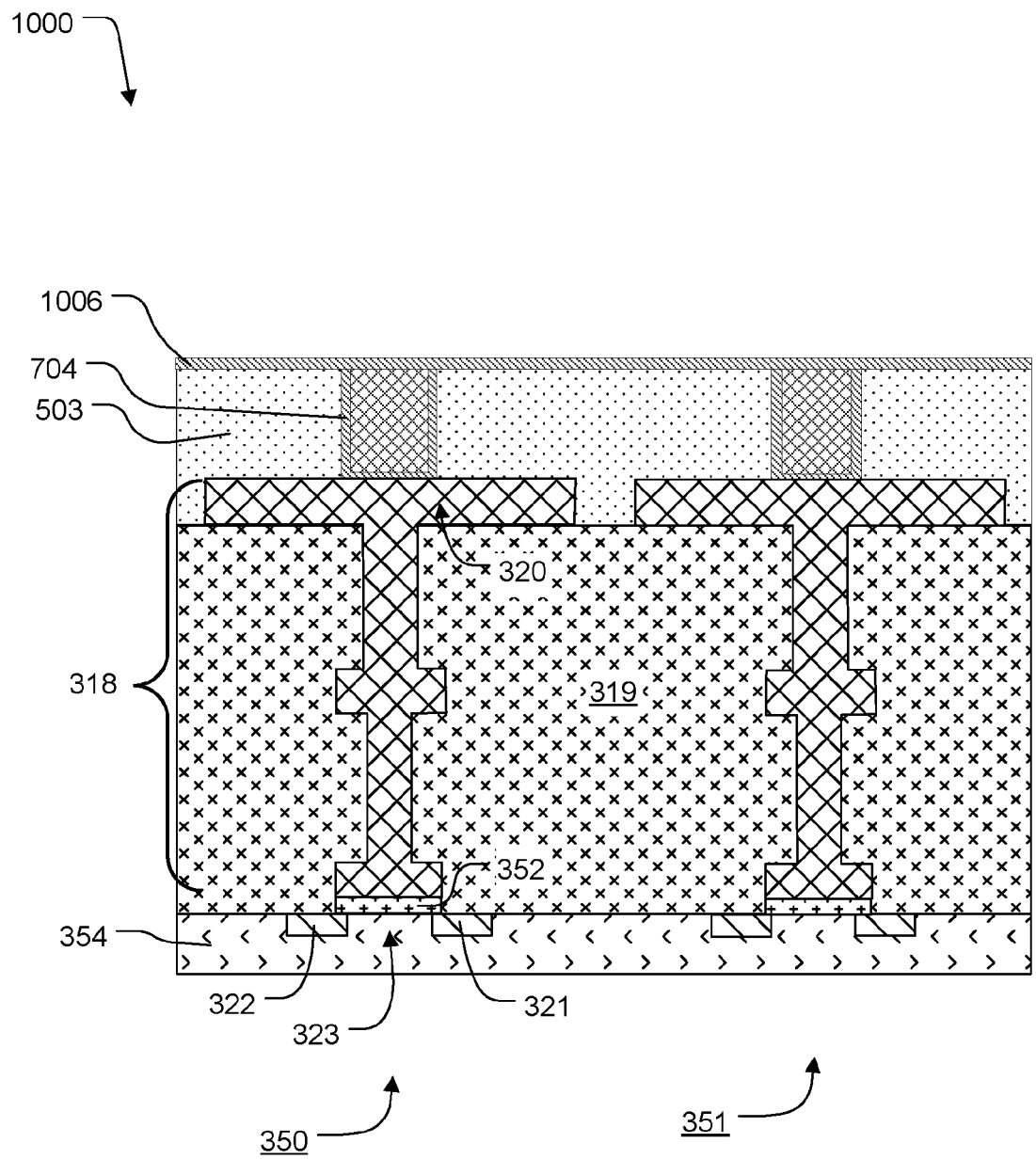

Next, a layer of conductive material 805 such as tungsten, for example, is deposited on the structure 700 illustrated in FIG. 7, resulting in the structure 800 illustrated in FIG. 8. The conductive material 805 may be deposited using various techniques, such as sputtering, reactive sputtering, atomic layer deposition (ALD), low pressure chemical vapor deposition (LPCVD), plasma enhanced chemical vapor deposition (PECVD), metal organic chemical vapor deposition (MOCVD), etc. or any other suitable techniques. Next, conductive material 704 and conductive material 805 are planarized using a Chemical Mechanical Planarization (CMP) process, for example, resulting in the structure 900 illustrated in FIG. 9. As an optional, additional step, a via barrier liner 1006 may be formed on the planarized conductive material 704 and conductive material 805, resulting in the structure 1000 illustrated in FIG. 10. For example, the via barrier liner 1006 may be titanium nitride. While via barrier liner 1006 is illustrated in the FIGS. 11-14, via barrier liner 1006 is optional.

Figure 11:
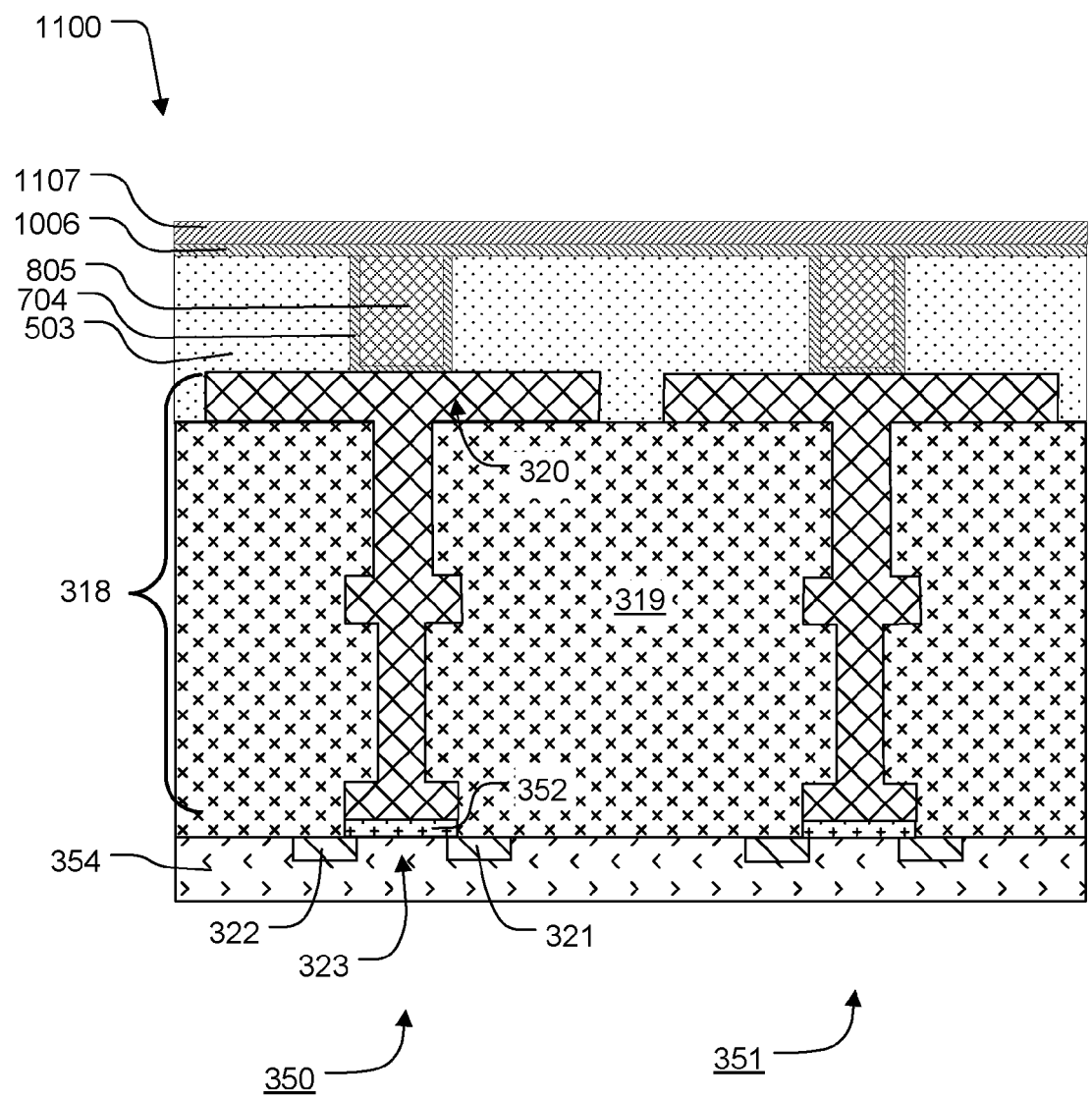

Next, a conductive material 1107 may be formed on the via barrier liner 1006, resulting in the structure 1100 illustrated in FIG. 11. Optionally, conductive material 1107 may be formed directly on the planarized conductive material 704 and conductive material 805. For example, the conductive material 1107 may be tantalum. Next, the conductive material 1107 is etched to form openings 1208, 1210, 1212 extending to the via barrier liner 1006, resulting in the structure 1200 illustrated in FIG. 12. The openings 1208, 1210, 1212 may, for example, be formed by using a lithographic process to pattern a layer of photoresist on the conductive material 1107 to define the locations of the openings 1208, 1210, 1212, and then anisotropically etching the dielectric material 503 using the patterned photoresist as an etch mask. The anisotropic etching of the conductive material 1107 may, for example, be a dry etch process, such as a fluorine based Reactive Ion Etching (RIE) process. In the illustrated embodiment, the openings 1208, 1210, 1212 are separated by a distance 1230L. Conductive element 1107 has a height 1230H. Length 1230L of conductive element 1107 is greater than length 320L of sensor plate 320. The thickness 1230H of conductive element 1107 is less than the thickness 320H of sensor plate 320. The spaces (i.e. 1220) between conductive material elements in conductive material 1107 are smaller than the spaces (i.e. 1220') between sensor plates. The conductive element need not be directly above and/or aligned with the uppermost floating gate conductor.

Figure 12:
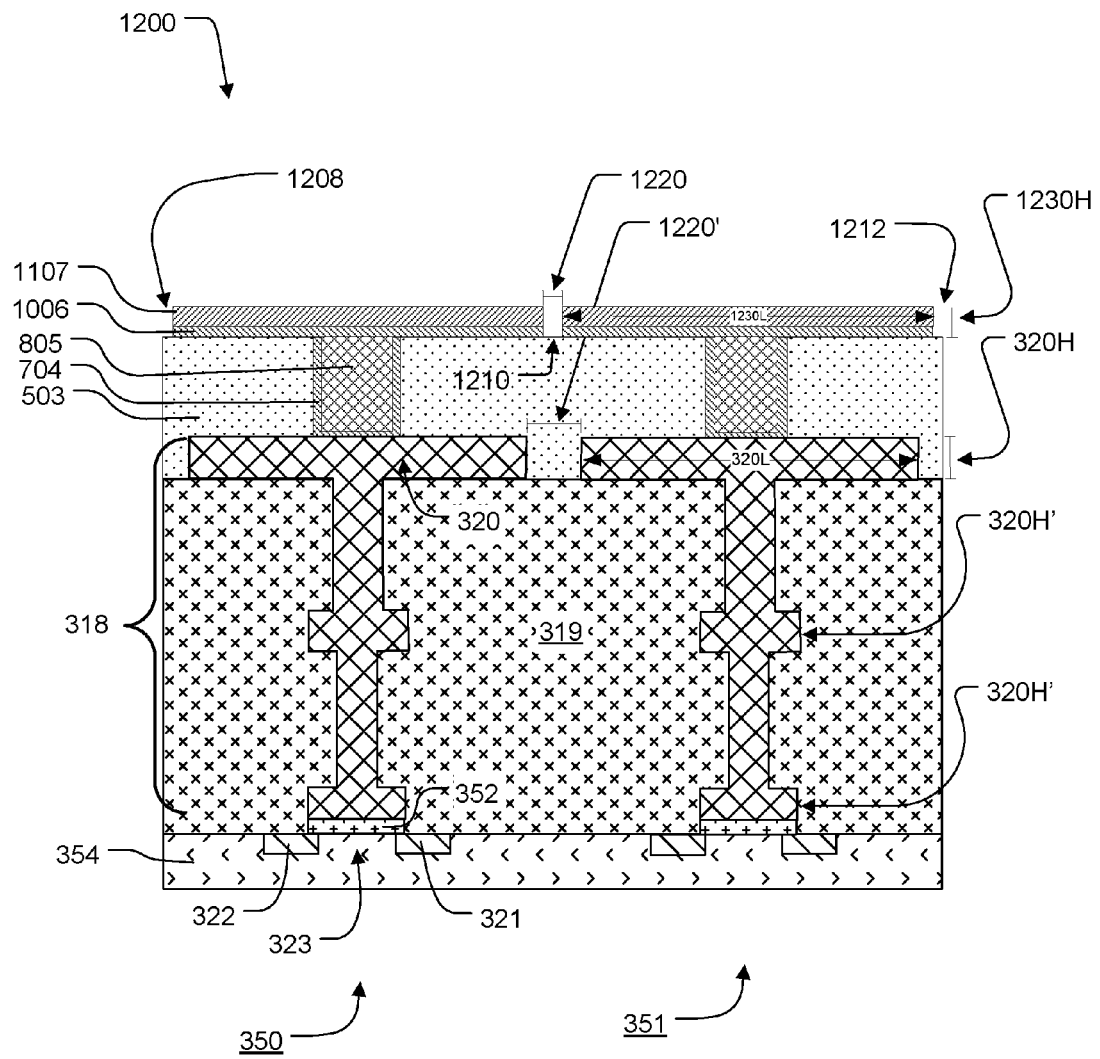
Figure 13:
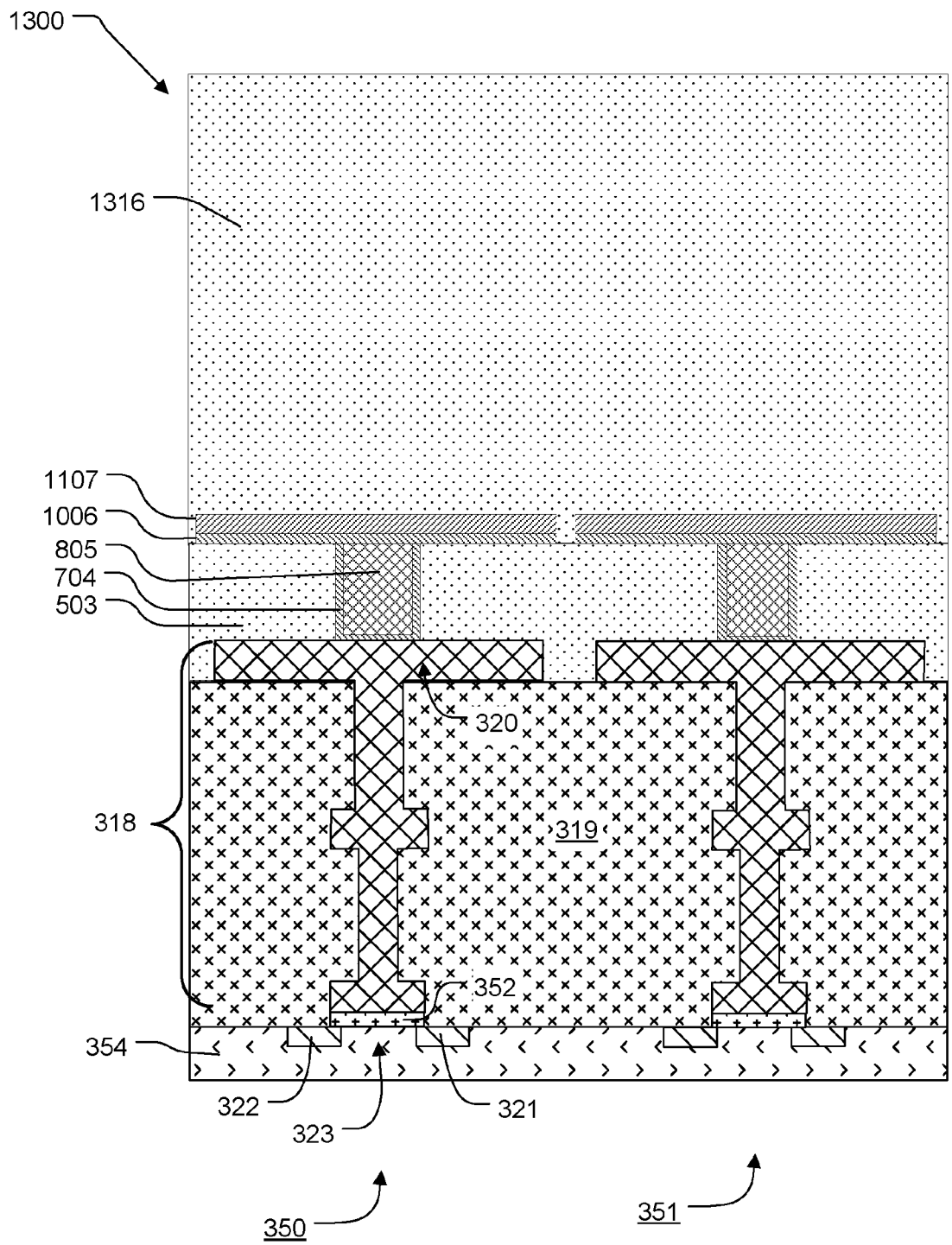
Figure 14:
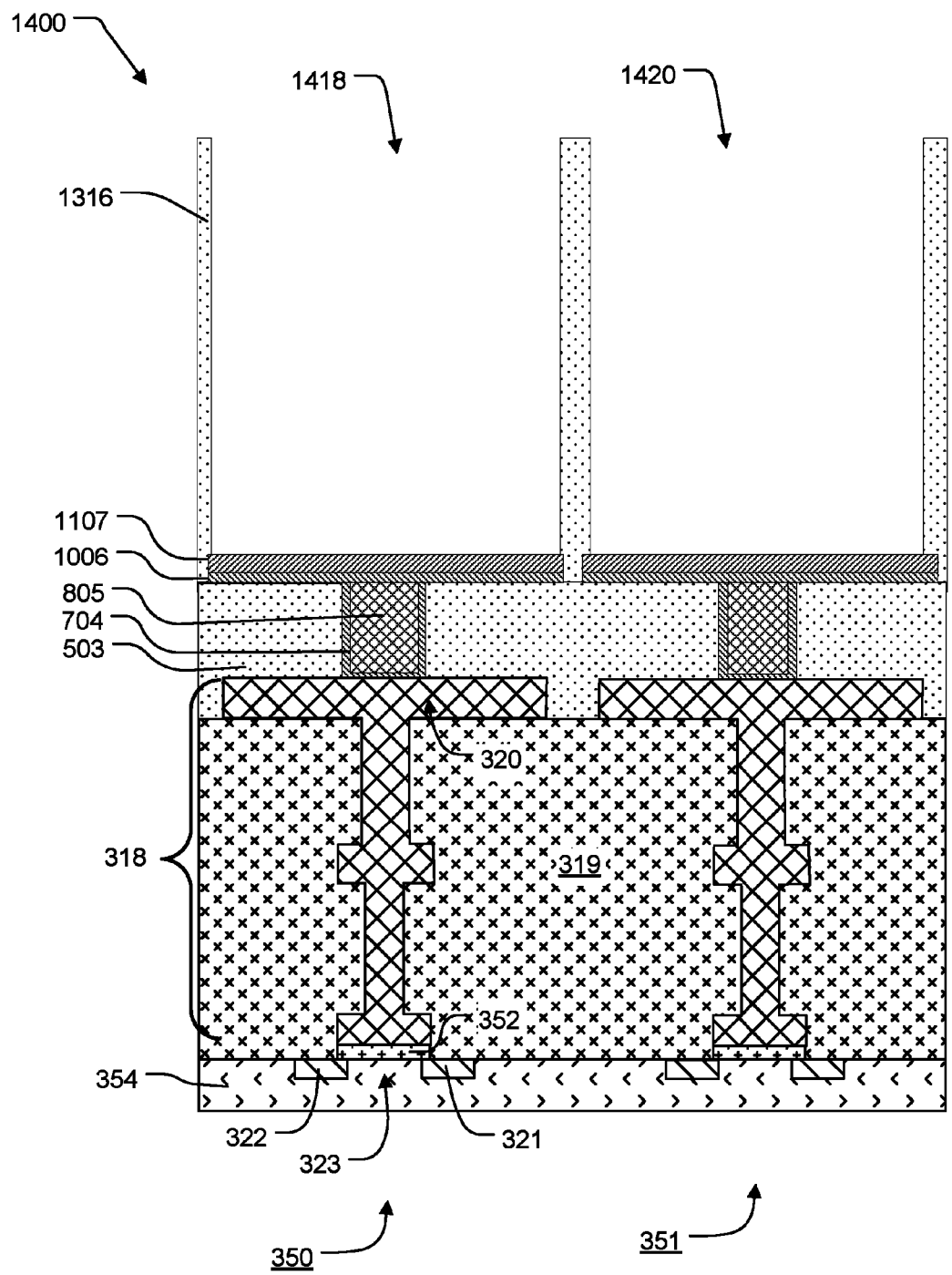

Next, a dielectric material 1316 may be formed on the structure 1200 illustrated in FIG. 12, resulting in the structure 1300 illustrated in FIG. 13. For example, the dielectric material 1316 may be tetraethyl orthosilicate, (TEOS) or silicon dioxide. Next, the dielectric material 1316 of the structure 1300 in FIG. 13 is etched to form openings 1418, 1420 extending to the upper surfaces of the floating gate structures of the chemical devices 350, 351, resulting in the structure 1400 illustrated in FIG. 14.

Figure 15:
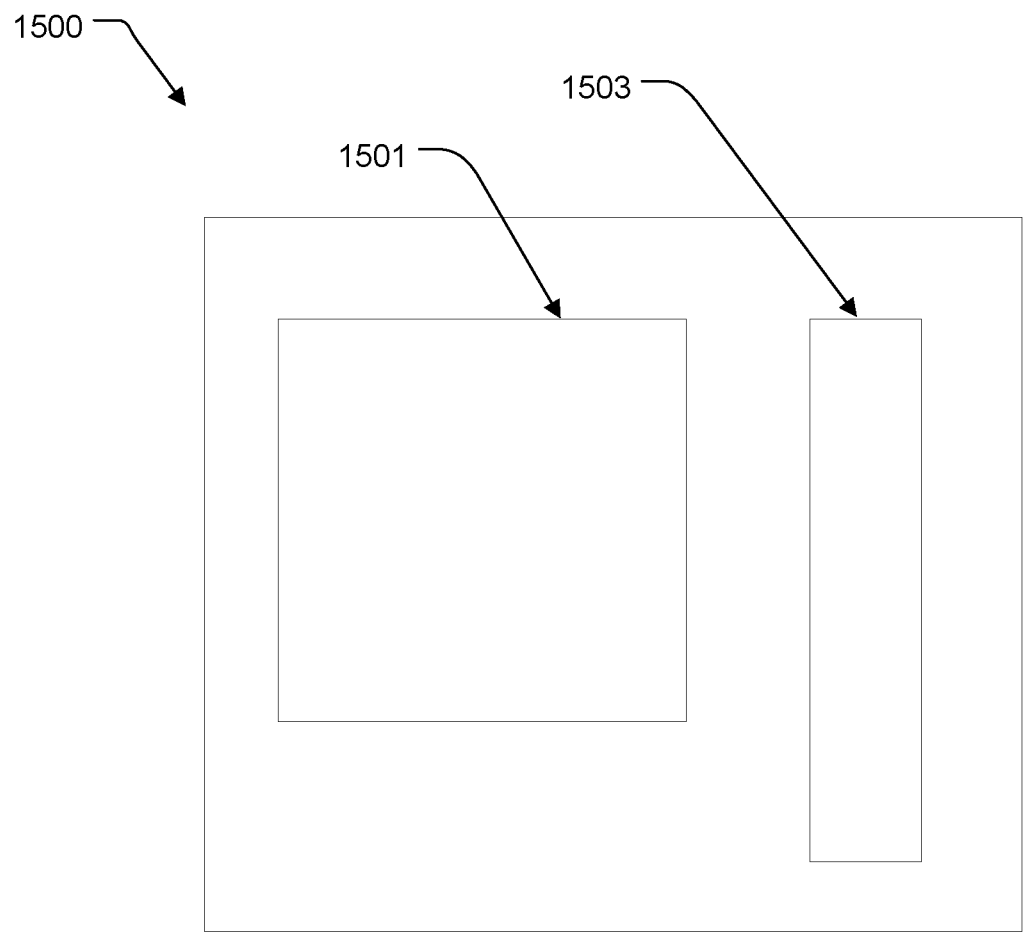
FIG. 15 illustrates a block diagram of an exemplary chemical device including an exemplary sensor region and an exemplary peripheral region, according to an exemplary embodiment.

FIG. 15 illustrates a block diagram of an exemplary chemical device including an exemplary sensor region and an exemplary peripheral region, according to an embodiment. The chemical device 1500 may include a sensor region 1501 containing the chemically-sensitive field effect transistor and a peripheral region 1503 containing peripheral circuitry to obtain a signal from the chemically-sensitive field effect transistor. In one embodiment, the conductive element is within a conductive layer that is only within the sensor region 1501. In another embodiment, the conductive element comprises a material not within the peripheral region 1503. The sensor region and peripheral region illustrated in FIG. 15 are not meant to be limiting as to shape or size or location, for example, on the chemical device.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

The invention claimed is:

1. A chemical device, comprising:
   a chemically-sensitive field effect transistor including a floating gate structure comprising plurality of floating gate conductors electrically coupled to one another;
   a dielectric layer overlying the floating gate structure;
   a conductive via formed through the dielectric layer and in electrical communication with an uppermost floating gate conductor of the plurality of floating gate conductors, the conductive via having a width less than the uppermost floating gate conductor;
   a conductive element overlying and in communication with the uppermost floating gate conductor in the plurality of floating gate conductors through the conductive via, the conductive element wider and thinner than the uppermost floating gate conductor; and
   a dielectric material defining an opening extending to an upper surface of the conductive element.

2. The chemical device of claim 1, wherein the conductive element comprises at least one of titanium, tantalum, titanium nitride, and aluminum, and/or oxides and/or mixtures thereof.

3. The chemical device of claim 1, further comprising a second conductive element, wherein the distance between the conductive element and the second conductive element in the chemical device is about 0.18 microns.

4. The chemical device of claim 1, wherein the thickness of the conductive element is about 0.1-0.2 microns.

5. The chemical device of claim 1, wherein the uppermost floating gate conductor in the plurality of floating gate conductors has a thickness greater than a thickness of other floating gate conductors in the plurality of floating gate conductors.

6. The chemical device of claim 1, wherein the conductive element comprises a material different from a material comprising the uppermost floating gate conductor.

7. The chemical device of claim 1, wherein an inner surface of the dielectric material and the upper surface of the conductive element define an outer surface of a reaction region for the chemical device.

8. The chemical device of claim 1, wherein the plurality of floating gate conductors is within a layer that includes array lines and bus lines.

9. The chemical device of claim 1, including a sensor region containing the chemically-sensitive field effect transistor and a peripheral region containing peripheral circuitry to obtain a signal from the chemically-sensitive field effect transistor.

10. The chemical device of claim 9, wherein the conductive element is within a conductive layer that is only within the sensor region.

11. The chemical device of claim 9, wherein the conductive element comprises a material not within the peripheral region.

12. The chemical device of claim 1, wherein the floating gate structure comprising the plurality of floating gate conductors electrically coupled to one another and separated by dielectric layers.

13. The chemical device of claim 1, wherein a first layer of the dielectric material is silicon nitride and a second layer is at least one of silicon dioxide and tetraethyl orthosilicate, and the second layer defines sidewalls of the opening.

14. The chemical device of claim 1, further comprising:
   a microfluidic structure in fluid flow communication with the chemically-sensitive field effect transistor, and arranged to deliver analytes for sequencing.

15. The chemical device of claim 1, further comprising a conductive barrier layer overlying the conductive via and dielectric layer and underlying the conductive element.

16. The chemical device of claim 1, further comprising a conductive barrier layer disposed between the uppermost floating gate conductor and a conductive material of the conductive via, the conductive barrier layer further disposed between the dielectric layer and the conductive material of the conductive via.

17. A method for manufacturing a chemical device, the method comprising:
   forming a chemically-sensitive field effect transistor including a floating gate structure comprising a plurality of floating gate conductors electrically coupled to one another;
   forming a dielectric layer overlying the floating gate structure;
   forming a conductive via formed through the dielectric layer and in electrical communication with an uppermost floating gate conductor of the plurality of floating gate conductors, the conductive via having a width less than the uppermost floating gate conductor;
   forming a conductive element overlying and in communication with the uppermost floating gate conductor in the plurality of floating gate conductors through the conductive via, the conductive element wider and thinner than the uppermost floating gate conductor; and
   forming a dielectric material defining an opening extending to an upper surface of the conductive element.

18. The method for manufacturing a chemical device of claim 17, wherein the upper surface of the conductive element defines a bottom surface of a reaction region for the chemical device.

19. The method for manufacturing a chemical device of claim 17, wherein an inner surface of the dielectric material and the upper surface of the conductive element define an outer boundary of a reaction region for the chemical device.

20. The method for manufacturing a chemical device of claim 17, wherein the conductive element is formed within a conductive layer that is only within a sensor region of the chemical device.

* * * * *